(12) United States Patent
Watanabe

(10) Patent No.: US 11,874,454 B2
(45) Date of Patent: Jan. 16, 2024

(54) OPTICAL SCANNING APPARATUS AND IMAGE PICKUP APPARATUS

(71) Applicant: Evident Corporation, Nagano (JP)

(72) Inventor: Satoshi Watanabe, Fussa (JP)

(73) Assignee: Evident Corporation, Nagano (JP)

( * ) Notice: Subject to any disclaimer, the term of this patent is extended or adjusted under 35 U.S.C. 154(b) by 554 days.

(21) Appl. No.: 17/126,418

(22) Filed: Dec. 18, 2020

(65) Prior Publication Data

US 2021/0181495 A1 Jun. 17, 2021

Related U.S. Application Data

(63) Continuation of application No. PCT/JP2018/024526, filed on Jun. 28, 2018.

(51) Int. Cl.
*G02B 23/24* (2006.01)
*A61B 1/00* (2006.01)
(Continued)

(52) U.S. Cl.
CPC ...... *G02B 23/2453* (2013.01); *A61B 1/00165* (2013.01); *A61B 1/00172* (2013.01);
(Continued)

(58) Field of Classification Search
CPC ...... G02B 3/14; G02B 23/2453; G02B 23/26; G02B 23/2469; G02B 26/06; A61B 1/00165; A61B 1/00172; A61B 1/043
See application file for complete search history.

(56) References Cited

U.S. PATENT DOCUMENTS

| | | |
|---|---|---|
| 5,716,324 A | 2/1998 | Toida |
| 2011/0137126 A1 | 6/2011 | French et al. |
| 2018/0011309 A1* | 1/2018 | Andresen ............... G02B 6/06 |

FOREIGN PATENT DOCUMENTS

| | | |
|---|---|---|
| JP | 06-63048 A | 3/1994 |
| JP | 06-70881 A | 3/1994 |

(Continued)

OTHER PUBLICATIONS

International Search Report dated Sep. 18, 2018 received in PCT/JP2018/024526.

(Continued)

*Primary Examiner* — Daniel Petkovsek
(74) *Attorney, Agent, or Firm* — Scully, Scott, Murphy & Presser, P.C.

(57) ABSTRACT

An optical scanning apparatus includes: a light source that emits light; a basic wavefront modulator that performs spatial light phase modulation on incident light on an optical path from the light source to an incident end surface of a fiber, to thereby generate light having a basic wavefront and emit the generated light, the light having the basic wavefront being to be incident on the incident end surface for obtaining, by light emitted from an emission end surface of the fiber, illumination light having a basic intensity distribution; and a two-dimensional intensity distribution control apparatus configured to change the basic intensity distribution by emitting light for causing light in which a phase distribution of the basic wavefront is controlled to be incident on the incident end surface of the fiber.

14 Claims, 11 Drawing Sheets

(51) Int. Cl.
   *A61B 1/04* (2006.01)
   *G02B 23/26* (2006.01)
(52) U.S. Cl.
   CPC .............. *A61B 1/043* (2013.01); *G02B 23/26* (2013.01); *G02B 23/2469* (2013.01)

(56) References Cited

FOREIGN PATENT DOCUMENTS

| | | |
|---|---|---|
| JP | 2005-328990 A | 12/2005 |
| JP | 2011-527218 A | 10/2011 |
| JP | 2016-109579 A | 6/2016 |
| JP | 2016-202360 A | 12/2016 |
| WO | 2010/004297 A1 | 1/2010 |
| WO | WO-2016207881 A1 * 12/2016 | ............... A61B 1/00 |
| WO | 2017/174596 A1 | 10/2017 |

OTHER PUBLICATIONS

Japanese Office Action dated Jan. 12, 2022 received in 2020-526798.
Written Opinion of the International Searching Authority dated Sep. 18, 2018 received in PCT/JP2018/024526.

* cited by examiner

OPTICAL SCANNING APPARATUS AND IMAGE PICKUP APPARATUS

CROSS-REFERENCE TO RELATED APPLICATIONS

This application is a continuation application of PCT/JP2018/024526 filed on Jun. 28, 2018, the entire contents of which are incorporated herein by this reference.

BACKGROUND OF THE INVENTION

1. Field of the Invention

The present invention relates to an optical scanning apparatus and an image pickup apparatus that use a multi-core fiber.

2. Description of the Related Art

In recent years, illumination apparatuses and image pickup apparatuses, which are configured to transmit light by using optical fibers, have been developed. For example, fiber scopes that transmit optical images by bundled optical fibers have been put into practical use. However, in fiber scopes, each one of optical fibers corresponds to each pixel and resolution is specified by the number of fiber bundles, and as a result, definition of images that can be transmitted by the fiber scopes is relatively low.

In view of the above, an image pickup apparatus provided with a distal end scanner has been developed as an apparatus for acquiring high-definition images. Such an image pickup apparatus including a distal end scanner generates spot illumination (light spot) by optical fibers to perform scanning with the light spot (point scanning). Then, the image pickup apparatus illuminates an object by point scanning, and sequentially captures optical images of the object acquired by the illumination, to acquire an image for a whole screen.

However, an image pickup apparatus provided with a distal end scanner is required to include a scanning mechanism for performing scanning with a light spot, at the distal end from which illumination light is emitted. Such a configuration makes it difficult to reduce the size of the apparatus.

In view of the above, an image pickup apparatus provided with a multi-mode fiber or a multi-core fiber including bundled single-mode fibers has been developed as a high-definition and compact image pickup apparatus. For example, Japanese Unexamined Patent Application Publication No. 2011-527218 discloses an endoscope configured to adjust a phase of incident light that enters a multi-mode fiber or fiber bundles using a spatial light phase modulator and to perform point scanning with a light spot. Note that, as the spatial light phase modulator, the one using a liquid crystal panel is commonly used.

In addition, Japanese Patent Application Laid-Open Publication No. 2016-202360 discloses an apparatus configured to perform high-resolution imaging by illuminating a specimen with an arbitrary and high-resolution light intensity pattern regardless of bending of optical fibers by adding a fiber Bragg grating to a plurality of single-mode fiber bundles to thereby detect the bending of the optical fibers based on a wavelength shift of reflected waves, and by adjusting, based on the detected bending, a wavefront of light from a spatial light phase modulator.

Note that, in apparatuses (point scanning image pickup apparatuses) configured to illuminate an object while scanning the object with a light spot and detect a local optical response (reflection, fluorescence) of the object to form an image, the time required for image acquisition is determined based on a scanning rate of the light spot and the number of scanning points.

Among the point scanning image pickup apparatuses, when an apparatus configured to perform point scanning with a light spot by using a spatial light phase modulator is used, a scanning position is determined by controlling an oriented state of a liquid crystal panel that configures the spatial light phase modulator.

SUMMARY OF THE INVENTION

An optical scanning apparatus according to one aspect of the present invention includes: a light source that emits light; a fiber including a plurality of cores each having one or more propagation modes including a single mode or a few modes, the fiber being configured to transmit light between a first end surface and a second end surface, the first end surface being configured by one end surfaces of the plurality of cores, the second end surface being configured by other end surfaces of the plurality of cores; a basic wavefront modulator configured to perform spatial light phase modulation on incident light on an optical path from the light source to the first end surface, to thereby generate light having a basic wavefront and emit the generated light, the light having the basic wavefront being to be incident on the first end surface for obtaining, by light emitted from the second end surface of the fiber, illumination light having a basic intensity distribution at a position with a predetermined distance from the second end surface; and a two-dimensional intensity distribution control apparatus configured to change the basic intensity distribution by emitting, on the optical path from the light source to the first end surface, light for causing light in which a phase distribution of the basic wavefront is controlled to be incident on the first end surface of the fiber.

An image pickup apparatus according to one aspect of the present invention includes the optical scanning apparatus and a photoelectric conversion apparatus configured to receive at least one of reflected light and fluorescence from an object illuminated with the illumination light emitted from the second end surface and convert the at least one of the reflected light and fluorescence into an electric signal.

Furthermore, an image pickup apparatus according to another aspect of the present invention includes: a light source that emits light; a fiber including a plurality of cores each having one or more propagation modes including a single mode or a few modes, the fiber being configured to transmit light between a first end surface and a second end surface, the first end surface being configured by one end surfaces of the plurality of cores, the second end surface being configured by other end surfaces of the plurality of cores; a first basic wavefront modulator configured to receive emitted light from the light source and perform spatial light phase modulation on the received emitted light, to thereby generate light having a first basic wavefront and emit the generated light, the light having the first basic wavefront being to be incident on the first end surface for obtaining, by light emitted from the second end surface of the fiber, illumination light having a basic intensity distribution at a first position in a first region with a predetermined distance from the second end surface; a second basic wavefront modulator configured to receive the emitted light from the light source, and perform spatial light phase modulation on the received emitted light, to thereby generate light having a second basic wavefront and emit the generated light, the light having the second basic wavefront being to be incident on the first end surface for obtaining, by light emitted from the second end surface of the fiber, illumination light having a basic intensity distribution at a second position in a second region with a predetermined distance from the second end surface, the second position corresponding to the first position; a first region information adding apparatus configured to add information indicating the first region to the light having the first basic wavefront; a second region information adding apparatus configured to add information indicating the second region to the light having the second basic wavefront; a photoelectric conversion apparatus configured to receive at least one of reflected light and fluorescence from an object illuminated with the illumination light emitted from the second end surface and convert the at least one of the reflected light and the fluorescence into an electric signal; and a region information detection apparatus configured to detect an electric signal based on light from the first region and an electric signal based on light from the second region separately, based on the information added by the first region information adding apparatus and the information added by the second region information adding apparatus.

DETAILED DESCRIPTION OF THE PREFERRED EMBODIMENTS

Hereinafter embodiments of the present invention are described in detail with reference to drawings.

First Embodiment

Figure 1:
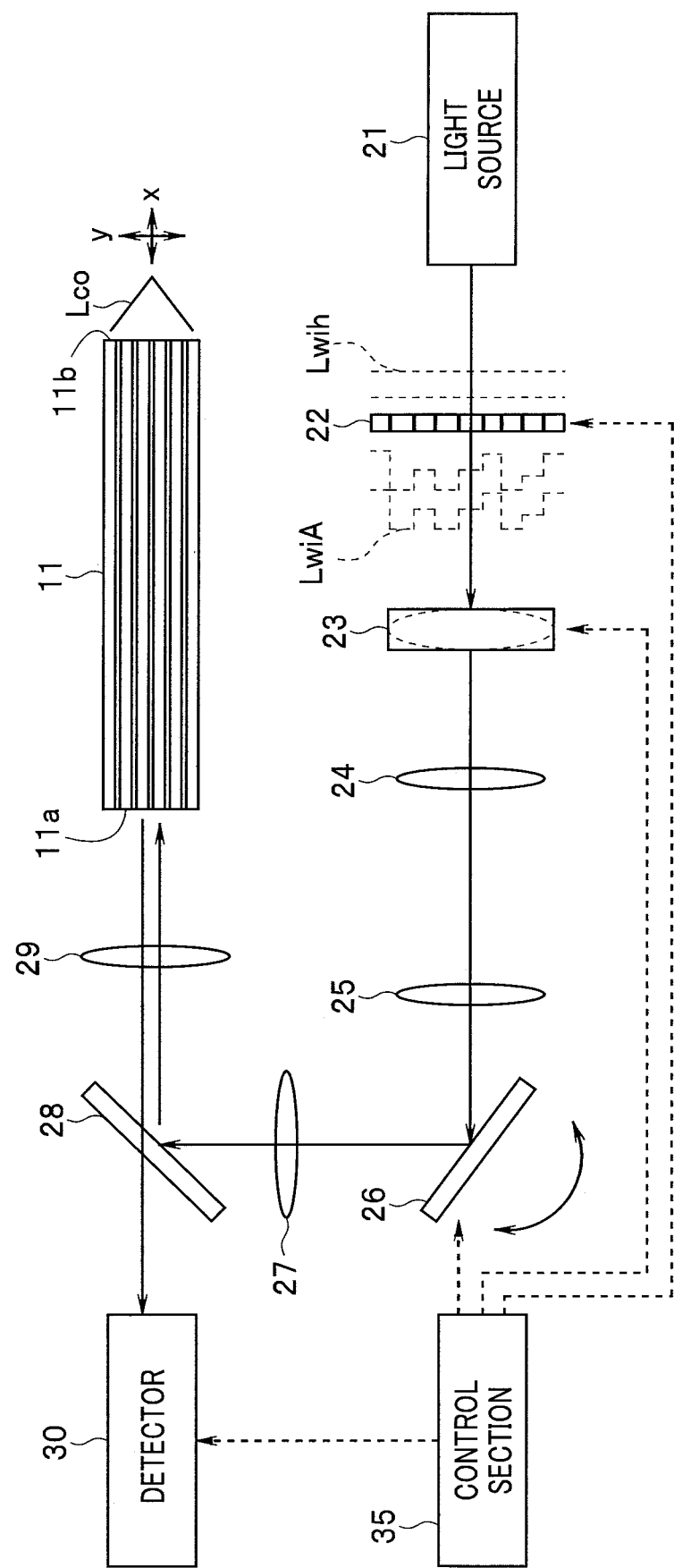
FIG. 1 is an explanatory view illustrating an image pickup apparatus using an optical scanning apparatus according to a first embodiment of the present invention.

FIG. 1 is an explanatory view illustrating an image pickup apparatus using an optical scanning apparatus according to the first embodiment of the present invention.

The present embodiment uses a multi-core fiber (hereinafter, also referred to as a wavefront transmission unit) including a plurality of cores each having one or a few propagation modes (single mode or a few modes). In the present embodiment, a basic wavefront modulator configured by a spatial light phase modulator is used to cause a light spot to emit from an emission end of the wavefront transmission unit and point scanning is performed by using a condensing position control section configured to control a condensing position of the light spot. As a result, the frame rate of the point scanning depends not on modulation processing by the spatial light phase modulator but on the control of the condensing position by the condensing position control section. In the present embodiment, the condensing position control section is configured by a galvano mirror, for example, to achieve high-speed point scanning.

Note that the condensing position control section is configured to apply to an incident end surface of the wavefront transmission unit the light from the basic wavefront modulator by changing a phase distribution of the light. The condensing position control section can be referred to as a phase converter or a phase distribution control section. In addition, the condensing position control section consequently changes an intensity distribution (hereinafter, referred to as a basic intensity distribution) of the light that forms the light spot, and can be referred to as an intensity distribution control section.

First, with reference to the explanatory views in FIGS. 2 to 4, description will be made on the image pickup principle utilizing the wavefront transmission unit configured by the multi-core fiber.

Figure 2:
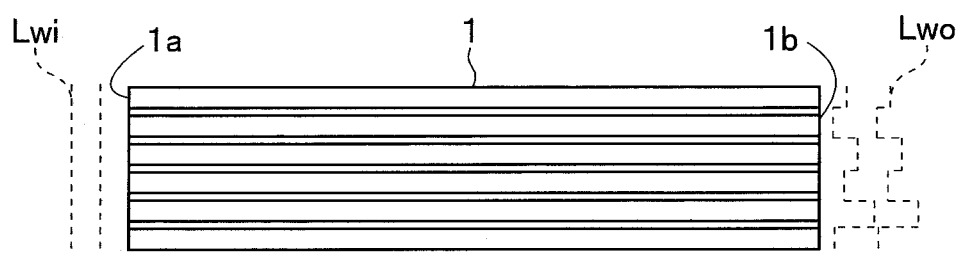
FIG. 2 is an explanatory view for describing an image pickup principle utilizing a wavefront transmission unit configured by a multi-core fiber.

In FIG. 2, the wavefront transmission unit 1 is configured by the multi-core fiber including a plurality of cores each having one or a few propagation modes (single mode or a few modes). FIG. 2 schematically illustrates the cross section of the multi-core fiber that configures the wavefront transmission unit 1, and a rectangular represents one core. One ends of the respective cores are fixed to each other, and the other ends of the respective cores are also fixed to each other, to thereby configure a first end surface 1a of the wavefront transmission unit 1 as one end surface formed by all the one ends of the respective cores and configure a second end surface 1b of the wavefront transmission unit 1 as one end surface formed by all the other ends of the respective cores.

For example, a laser is used as a light source. The light from the laser is made to be incident from the first end surface 1a of the wavefront transmission unit 1. The light incident on the wavefront transmission unit 1 is dispersed by the respective cores, propagates in the cores, to be emitted from the second end surface 1b to illuminate an object. The light emitted from the second end surface 1b interferes with emitted light from each of other cores, as getting away from the second end surface 1b, to become a combined light.

Now it is supposed that a plane wave whose wavefront is parallel to the first end surface 1a is incident on the first end surface 1a of the wavefront transmission unit 1. The dashed lines in FIG. 2 illustrate that a wavefront Lwi of an incident wave (hereinafter, also referred to as incident wavefront) at the first end surface 1a is a plane. Normally, the optical path lengths from the incident end to the emission end of the multi-core fiber that configures the wavefront transmission unit 1 are not strictly equal to one another among the respective cores due to a degree of uniformity of the refractive index of the material, manufacturing variation, or the like. Therefore, the wavefront of the light incident from the first end surface 1a to be transmitted through each of the respective cores generates a phase amount depending on a propagation optical path length to the second end surface 1b. As a result, as illustrated by the dashed lines in FIG. 2, the wavefront (hereinafter, also referred to as emitted wavefront) Lwo at the second end surface 1b of the light emitted from the second end surface 1b is not a plane. Accordingly, when the incident light on the wavefront transmission unit 1 is laser, the light of a pattern having a random intensity distribution, which is generally observed as a speckle, is applied to the object from the second end surface 1b.

When the light having a first wavefront is made to be incident on the first end surface of the multi-core fiber, the light having a second wavefront is emitted from the second end surface. In this case, if it is supposed that the relative phase amounts among the respective cores configuring the multi-core fiber are fixed, when the light having, as an incident wavefront, a wavefront whose phase is opposite to the phase of the second wavefront is incident on the first end surface of the multi-core fiber, the light having the first wavefront is emitted from the second end surface.

The relative phase differences among the respective cores of the multi-core fiber can be measured in advance. Therefore, if the light having, as the incident wavefront, the wavefront whose phase is opposite to the phase of the wavefront Lwo in FIG. 2 is incident on the first end surface 1a by using a spatial light phase modulator, a plane wave can be emitted from the second end surface 1b. Furthermore, a spherical component is added to the incident wavefront, to thereby cause the light from the second end surface to condense, to enable a light spot to be obtained at a position with a predetermined distance from the second end surface.

Figure 3:
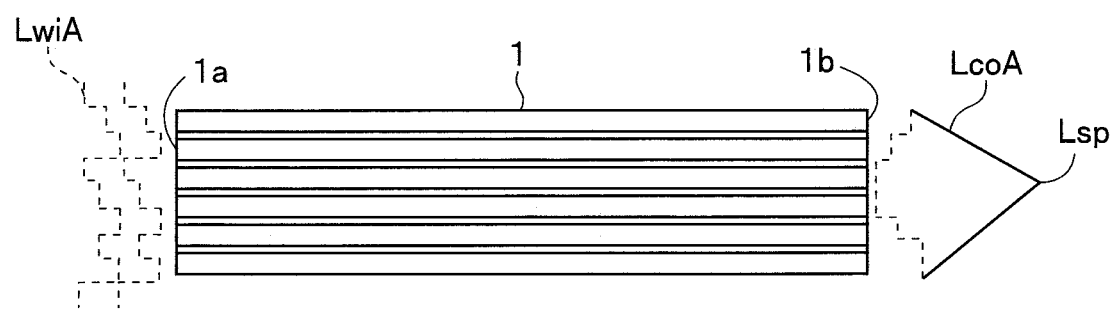
FIG. 3 is an explanatory view for describing the image pickup principle utilizing the wavefront transmission unit configured by the multi-core fiber.

FIG. 3 illustrates the above-described state. The incident wavefront LwiA is obtained by adding the spherical component to the wavefront whose phase is opposite to the phase of the wavefront Lwo in FIG. 2. This causes the emitted light LcoA from the second end surface 1b of the wavefront transmission unit 1 to form a light spot Lsp at a predetermined position. Note that the relative phase differences among the respective cores of the multi-core fiber may be obtained by actual measurement, or may be obtained by generating a light spot at an arbitrary position on the other end side by another optical system, measuring the wavefront of the light in a case where the light transmits through the multi-core fiber in a reversed direction, and performing sign inversion of the measurement result (electronic phase conjugation).

Therefore, point scanning is performed on the emission end side to measure wavefronts with such a method, to thereby be capable of creating a lookup table based on which the spatial light phase modulator can generate the wavefronts enabling the point scanning. However, as described above, in the case where the light for enabling the point scanning is generated by the spatial light phase modulator, there is a disadvantage that the scanning rate is reduced depending on the frame rate of the liquid crystal panel that configures the spatial light phase modulator.

Figure 4:
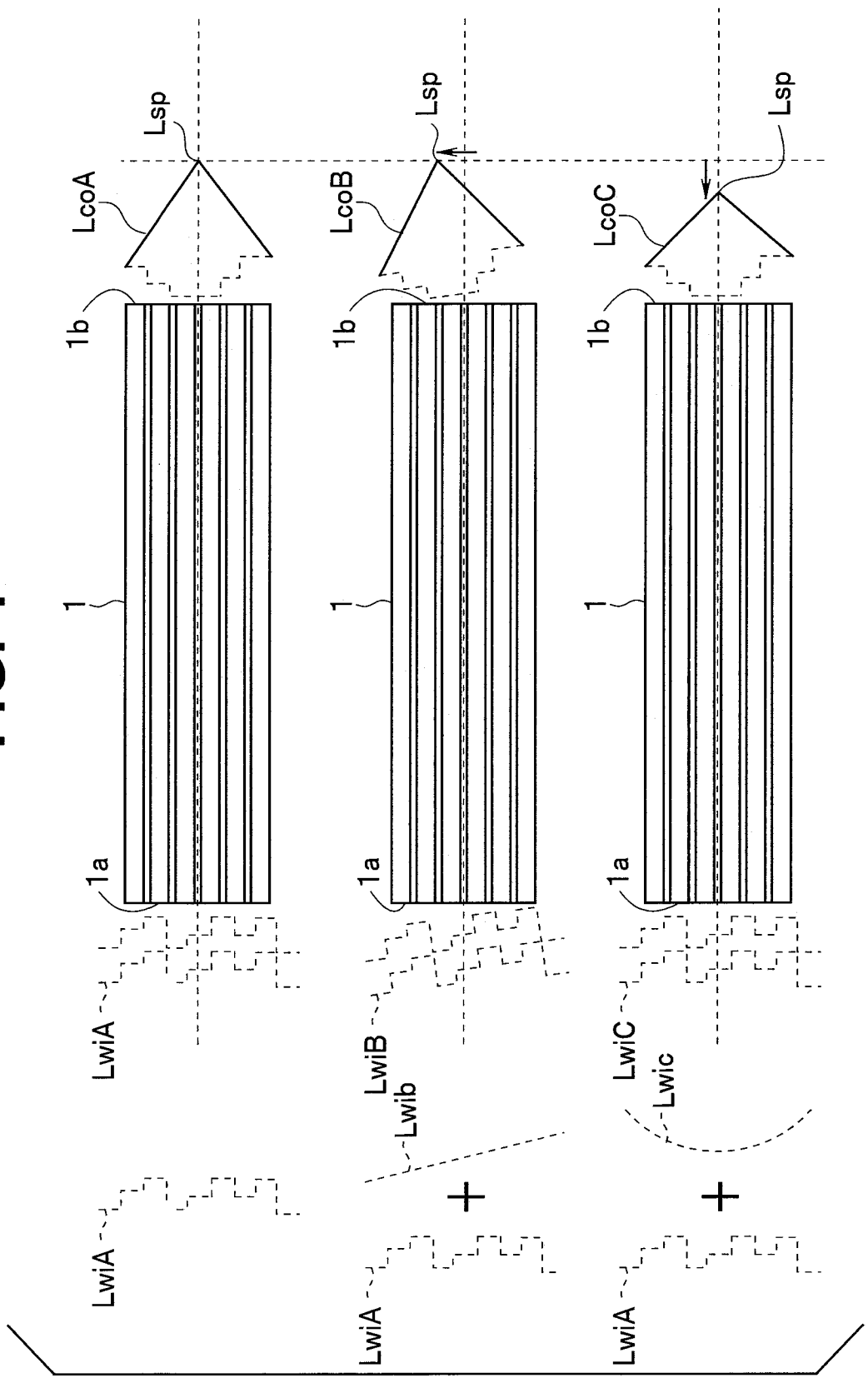
FIG. 4 is an explanatory view for describing a high-speed point scanning according to the first embodiment.

In view of the disadvantage, the present embodiment achieves high-speed point scanning by the method illustrated in FIG. 4.

Principle of High-Speed Point Scanning

The relative phase differences among the respective cores of the multi-core fiber change due to factors such as processing conditions, a temperature, a stress, and the like. Therefore, a shape of incident wavefront required for offsetting the phase differences among the respective cores is complicated, which results in a necessity for using the spatial light phase modulator capable of generating light having a desired wavefront at a high degree of freedom.

The upper part of FIG. 4 illustrates, similarly as FIG. 3, that the light having the wavefront LwiA is generated by the spatial light phase modulator, not illustrated, to cause the light having the incident wavefront LwiA to be incident on the first end surface 1a, to thereby be capable of obtaining a basic intensity distribution that forms the light spot Lsp at the position with a predetermined distance from the second end surface 1b. Hereinafter, the wavefront of the light to be incident on the first end surface 1a for obtaining the basic intensity distribution that forms the light spot Lsp at a predetermined point is referred to as a basic wavefront. The spatial light phase modulator for generating the light having the basic wavefront is referred to as a basic wavefront modulator. Note that the basic intensity distribution is not limited to the one forming the light spot, but may be the one forming light having a predetermined intensity pattern.

In the present embodiment, during a period in which an image for one screen is formed, for example, the setting of the basic wavefront modulator is not changed, and the light having the wavefront LwiA as the basic wavefront is emitted from the basic wavefront modulator. Then, the light having the wavefront LwiA is incident on the first end surface 1a by changing the angle of the light with respect to the optical axis by the condensing position control section.

The middle part of FIG. 4 illustrates the above-described state. A tilt component Lwib is added by the condensing position control section to the light having the wavefront LwiA emitted from the spatial light phase modulator, and as a result, the light having the wavefront LwiB obtained by the wavefront LwiA being tilted is incident on the first end surface 1a. In the example illustrated in FIG. 4, the phase of the wavefront of the light incident on the cores located on the lower side on the paper surface of the drawing progresses and the phase of the wavefront of the light incident on the cores on the upper side on the paper surface delays, and as a result, the light spot Lsp formed by the emitted light LcoB from the second end surface 1b is shifted to the upper side on the paper surface. Note that the addition of the tilt component by the condensing position control section causes the light from the basic wavefront modulator to be incident on the incident end surface of the wavefront transmission unit, with the phase distribution of the light being changed. As described above, the condensing position control section functions as the phase distribution control section.

Thus, a tilt angle to be added and a tilt direction are adjusted by the condensing position control section, to thereby be capable of causing the light spot Lsp to shift to a desired position to achieve the point scanning. The condensing position control section is configured by a galvano mirror, for example, to thereby be capable of changing the tilt component to be added at an extremely high speed. As a result, the point scanning can be achieved in an extremely short scanning time. Note that, when a surface on which the light spot Lsp exists and which is parallel to the second end surface 1b is supposed to be an xy plane, the light spot can be formed at an arbitrary position on the xy plane by the condensing position control illustrated in the middle part of FIG. 4.

Furthermore, the lower part of FIG. 4 illustrates that the condensing position of the light spot can be shifted in the optical axis direction. For example, a spherical component Lwic is added by the condensing position control section to the light having the wavefront LwiA from the spatial light phase modulator. As a result, the light having a wavefront LwiC obtained by the wavefront LwiA being bent is incident on the first end surface 1a. In the example illustrated in FIG. 4, the phase of the wavefront of the light incident on the cores on the peripheral side of the multi-core fiber progresses and the phase of the wavefront of the light incident on the cores on the center side of the multi-core fiber delays. As a result, the light spot Lsp formed by the emitted light LcoC from the second end surface 1b shifts to the second end surface 1b side. Note that the condensing position control section can be configured by a variable focal lens, for example.

Thus, the components to be added to the basic wavefront for controlling the condensing position of the light spot include the tilt component and the spherical component, and as the element that adds these components to the basic wavefront, an element with a relatively low degree of freedom of change can be used. In the present embodiment, the basic wavefront modulator and the condensing position control section are implemented by the devices different from each other. The major role of the basic wavefront modulator is to offset the relative phase differences among the respective cores of the multi-core fiber. The major role of the condensing position control section is to control the condensing position of the light spot (scanning control).

Next, description will be made on the configuration of the image pickup apparatus of the present embodiment with reference to FIG. 1.

In FIG. 1, the wavefront transmission unit 11 is configured by the multi-core fiber including a plurality of cores each having one or a few propagation modes (single mode or a few modes). FIG. 1 schematically illustrates the cross section of the multi-core fiber configuring the wavefront transmission unit 11, similarly as in FIG. 2, and each rectangular indicates one core. One ends of the respective cores are fixed to each other, and the other ends of the respective cores are also fixed to each other. The one ends of the respective cores collectively constitute a first end surface 11a of the wavefront transmission unit 11, and the other ends of the respective cores collectively constitute a second end surface 11b of the wavefront transmission unit 11.

Note that, when the multi-core fiber is configured by the cores aligned and arranged at equal intervals, a plurality of light spots Lsp are likely to be generated due to the alignment pitch (similarly as the high-order light via a grating). The wavefront transmission unit 11 may be configured such that spatial frequency components that are characteristic to the arrangement of the cores are not likely to be generated by arranging the cores in a random manner.

The control section 35 may be configured by a processor using a CPU and the like, and may operate according to a program stored in a memory, not illustrated, to control respective sections, or may implement a part of or all of the functions of the respective sections by an electronic circuit of hardware. The control section 35 is configured to control operations of: the basic wavefront modulator 22, to be described later, which configures a basic wavefront modulation section; a condensing position control section 23; a condensing position control section 26; and a detector 30.

The light source 21 is configured by a laser, for example. Note that the laser used as the light source 21 is preferably a gas laser using HeNe, or the like, or a single-mode semiconductor laser. The wavelength of the emitted light from the light source 21 is selected depending on a characteristic of an object and on a characteristic of a fluorescent probe when performing image pickup using fluorescence. It is preferable to appropriately select the time coherence of the light source 21 so that a combined wavefront is formed at the second end surface 11b.

On the optical path of the emitted light from the light source 21, the basic wavefront modulator 22, the condensing position control section 23, two lenses 24, 25, and the condensing position control section 26 are disposed. The basic wavefront modulator 22 is configured by the spatial light phase modulator, such as a transmissive liquid crystal array, a reflective liquid crystal array (LCOS) or the like, in which a plurality of pixels are arranged two-dimensionally. The basic wavefront modulator 22 is configured such that the number of pixels of these arrays is equal to or larger than at least the number of cores configuring the wavefront transmission unit 11. The basic wavefront modulator 22 is controlled by the control section 35 and configured to change retardation for the respective pixels in the arrays within a range of phase delay (retardation) of 0 to $2\pi$ in a desired gradation. Note that, when the basic wavefront modulator 22 is configured by a liquid crystal array, the polarization components to which retardation can be applied are limited. Therefore, the polarization of the light from the light source 21 may be limited to a direction in which the retardation can be changed. Alternatively, two spatial light phase modulators may be provided in accordance with the two polarization directions orthogonal to each other. In addition to the spatial light phase modulator, a spatial light intensity modulator may be provided. In that case, it is preferable that the spatial light phase modulator and the spatial light intensity modulator are disposed at positions optically conjugate to each other.

The light source 21 emits a plane wave Lwih. The basic wavefront modulator 22 receives the plane wave Lwih on the incident surface, and emits the light having the basic wavefront LwiA for forming the light spot at the position with the predetermined distance from the second end surface 11b on the plane (xy plane) which is parallel to the second end surface 11b of the wavefront transmission unit 11, for example.

The light having the basic wavefront LwiA passes through the condensing position control section 23 and the two lenses 24, 25, to be incident on the condensing position control section 26. The condensing position control section 23 can be configured by a variable focal lens, for example. The condensing position control section 23 is configured to change the condensing position of the light spot formed by the emitted light from the second end surface 11b of the wavefront transmission unit 11 in a direction (hereinafter, referred to as a z direction or a depth direction) orthogonal to the xy plane. In other words, the condensing position control section 23 is controlled by the control section 35 and configured to add the spherical component illustrated in the lower part of FIG. 4 to the basic wavefront. Note that the condensing position control section 23 is disposed so as to be conjugate to the first end surface 11a. The emitted light from the condensing position control section 23 is incident on the condensing position control section 26 through the lenses 24, 25.

The condensing position control section 26 is controlled by the control section 35 and configured to add the tilt component illustrated in the middle part of FIG. 4 to the basic wavefront. With the addition of the tilt component, the condensing position control section 26 changes the condensing position of the light spot formed by the emitted light from the second end surface 11b of the wavefront transmission unit 11 to an arbitrary position in the xy plane. Note that the condensing position control section 26 is configured to change the intensity distribution of the emitted light, which is obtained by the light having the basic wavefront, in the xy plane. The condensing position control section 26 can be referred to as a two-dimensional intensity distribution control section or a two-dimensional intensity distribution control apparatus. As the condensing position control section 26 that provides such an effect, a galvano mirror or a MEMS (Micro-Electro-Mechanical Systems) mirror can be used, for example. Note that the condensing position control section 23 is configured to change the basic intensity distribution that forms the light spot in the z direction. The condensing position control section 23 can be referred to also as a depth direction intensity distribution control section or a depth direction intensity distribution control apparatus.

In addition, the example illustrated in FIG. 1 illustrates that the position of the light spot is changed in the y direction, for example, with the arrow indicating that the condensing position control section 26 is configured to swing around one axis, not illustrated. However, the condensing position control section 26 is configured to swing around another axis, not illustrated, to enable the position of the light spot to change also in the x direction, for example.

When the condensing position control section 26 is configured by a galvano mirror, for example, the galvano mirror is configured to swing around the one axis, not illustrated, and the entirety of the apparatus including the galvano mirror is configured to swing around the other axis, not illustrated, to thereby be capable of forming the light spot at an arbitrary position on the xy plane. Alternatively, the condensing position control section 26 may be configured by a first galvano mirror configured to swing around the one axis, not illustrated, and a second galvano mirror configured to swing around the other axis, not illustrated. The condensing position control section 26 may reflect the incident light sequentially by the first galvano mirror and the second galvano mirror and emit the reflected light, to form the light spot at an arbitrary position on the xy plane. Furthermore, the condensing position control section 26 may be configured by a MEMS mirror configured to be capable of changing the angle of light in directions of two axes. Furthermore, the condensing position control section 26 may be configured to swing around the one axis, and a beam splitter 28, to be described later, may be configured to swing around the other axis, to thereby form the light spot at an arbitrary position on the xy plane. The beam splitter 28 is configured to reflect the emitted light from the condensing position control section 26.

The condensing position control section 26 is disposed so as to be conjugate to the first end surface 11a. When two mirrors are used to form the light spot at an arbitrary position on the xy plane, a relay optical system is disposed between the mirrors so that the rotational centers of the mirrors are conjugate to the first end surface 11a. Thus, the condensing position control section 26 is configured to operate to move the light spot such that point scanning is performed within a predetermined range on the xy plane.

A lens 27 and the beam splitter 28 are disposed on the optical path of the emitted light from the condensing position control section 26. The lens 27 guides the light from the condensing position control section 26 to the beam splitter 28. The beam splitter 28 is configured to reflect the emitted light from the condensing position control section 26 to guide the reflected light to the wavefront transmission unit 11, and configured to transmit the light from the wavefront transmission unit 11 to guide the transmitted light to the detector 30. A lens 29 and the wavefront transmission unit 11 are disposed on the optical path of the reflected light from the beam splitter 28. The lens 29 is configured to guide the reflected light from the beam splitter 28 to the first end surface 11a of the wavefront transmission unit 11. With such a configuration, the first end surface 11a of the wavefront transmission unit 11 receives the light having the basic wavefront or the light having a wavefront obtained by adding the tilt component or the spherical component to the basic wavefront (hereinafter, these wavefronts including the basic wavefront are referred also as a position-controlled wavefronts).

Note that a half mirror is used as the beam splitter 28 in the image pickup using normal light. A dichroic mirror is used as the beam splitter 28 in the image pickup using fluorescence.

The wavefront transmission unit 11 transmits the light incident on the first end surface 11a by each of the cores, to emit the light from the second end surface 11b. As a result that the light having the position-controlled basic wavefront has been incident on the first end surface 11a, the combined light Lco from the second end surface 11b is condensed to form the light spot. The position at which the light spot is formed is controlled in the scanning direction (xy direction) by the condensing position control section 26 and controlled in a direction orthogonal to the scanning direction by the condensing position control section 23. The condensing position control section 26 is configured by the galvano mirror or the MEMS mirror, to enable the point scanning with the light spot at a high speed.

The point scanning is performed with the light spot formed by the emitted light Lco from the wavefront transmission unit 11, and thereby the object is illuminated while being scanned with the light spot. The reflected light from the object (object-reflected light) is incident on the second end surface 11b, to be transmitted toward the first end surface 11a side by each of the cores of the wavefront transmission unit 11 and emitted from the first end surface 11a toward the lens 29 side. The emitted light transmits through the lens 29 and the beam splitter 28 to be incident on the detector 30. The detector 30 is configured, for example, by a photoelectric conversion section (photoelectric conversion apparatus) such as a photodiode which is a light detection element. The detector 30 is controlled by the control section 35 and configured to detect the incident light and generate an image signal based on an optical image formed by the incident light.

An example of the light detection element that configures the detector 30 includes the one considering a light reception sensitivity, noise, and a responsive speed depending on the wavelength of the light to be detected and the light quantity expected for the object-reflected light. Furthermore, as the light detection element that configures the detector 30, a single-pixel element or a two-dimensional image sensor may be used. In addition, the size of the light-receiving surface of the light detection element that configures the detector 30 is preferably large enough to fully receive the signal light.

In FIG. 1, the constituent elements except for the detector 30 configure the optical scanning apparatus.

Note that description has been made above on the example in which the condensing position control section 23 is disposed at a position on which the emitted light from the basic wavefront modulator 22 is incident. However, the condensing position control section 23 may be disposed at any position on the optical path extending from the light source 21 to the first end surface 11a of the wavefront transmission unit 11.

Description has been made on the example in which the variable focal lens is used as the condensing position control section 23. However, the condensing position control section 23 may be configured by a deformable mirror. For example, the mirror used as the galvano mirror that configures the condensing position control section 26 may be configured by a deformable mirror. In addition, the beam splitter 28 may be configured by a deformable mirror. In the case where the deformable mirrors are used, the deformable mirrors may additionally have a shape for correcting aberrations generated by the lens 27 and the lens 29.

Description has been made above on the example in which the condensing position control section 26 is configured by the galvano mirror and disposed on the optical path of the emitted light from the light source 21, for example. However, the condensing position control section can be configured by the beam splitter 28. In other words, a fixed mirror is disposed at the position of the condensing position control section 23 in FIG. 1, and the beam splitter 28 is moved in accordance with the scanning with the light spot.

Figure 5:
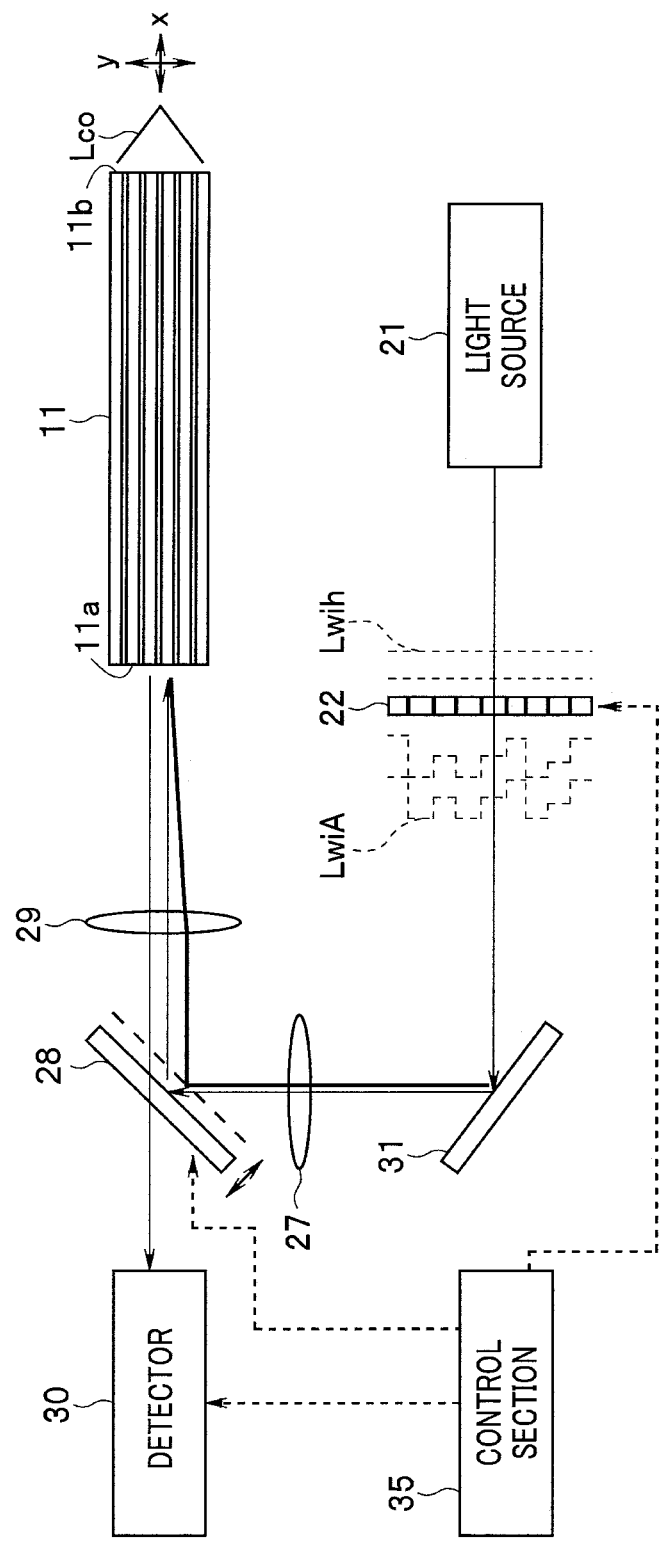
FIG. 5 is an explanatory view illustrating another configuration of a condensing position control section.

FIG. 5 is an explanatory view illustrating the configuration in such a case.

The basic wavefront modulator 22 and a mirror 31 are disposed on the optical path of the emitted light from the light source 21. The mirror 31 reflects the light having the basic wavefront from the basic wavefront modulator 22. The lens 27 and the beam splitter 28 are disposed on the optical path of the reflected light from the mirror 31. The lens 27 guides the light from the mirror 31 to the beam splitter 28. The beam splitter 28 reflects the emitted light from the mirror 31 to guide the reflected light to the wavefront transmission unit 11, and transmits the light from the wavefront transmission unit 11 to guide the transmitted light to the detector 30. In the example illustrated in FIG. 5, the beam splitter 28 can be moved in a direction orthogonal to the reflective surface as illustrated with the arrow in FIG. 5, by an actuator, not illustrated, controlled by the control section 35.

The light (illustrated by the bold line in FIG. 5) in the case where the reflective surface of the beam splitter 28 is located at the position illustrated by the dashed line is incident on the first end surface 11a of the wavefront transmission unit 11, with the wavefront of the light being tilted by the lens 29 with respect to the wavefront of the light (illustrated by the thin line arrow in FIG. 5) in the case where the reflective surface of the beam splitter 28 is located at the position illustrated by the solid line. Therefore, when the beam splitter 28 moves in the arrow direction in FIG. 5, the incident position where the light is incident on the lens 29 is changed. As a result, the tilt component to be added to the basic wavefront is changed, and the position of the light spot formed by the emitted light Lco from the second end surface 11b of the wavefront transmission unit 11 is changed in the y direction. Note that if the beam splitter 28 is moved in the direction perpendicular to the paper surface in FIG. 5, the position of the light spot formed by the emitted light Lco from the second end surface 11b of the wavefront transmission unit 11 can be changed in the x direction. In other words, by moving the beam splitter 28, point scanning can be performed with the light spot within a predetermined range on the xy plane. In this case, the beam splitter 28 is preferably disposed so as to coincide with the front side focal position of the lens 29 and the rear side focal position of the lens 27.

Next, the operation of the embodiment thus configured will be described with reference to the example in FIG. 1.

In order to carry out the point scanning, the basic wavefront is obtained in advance depending on the characteristics of the wavefront transmission unit 11. The light source 21 emits the plane wave Lwih. The plane wave is incident on the basic wavefront modulator 22. The basic wavefront modulator 22 is configured by a liquid crystal array, for example, and configured to convert the plane wave Lwih into the light having the basic wavefront LsiA by controlling the retardation of the respective pixels in the array and emits the light having the basic wavefront LwiA.

The light having the basic wavefront LwiA passes through the condensing position control section 23 and lenses 24, 25, to be incident on the condensing position control section 26. The condensing position control section 26 emits the light by adding a first tilt component to the incident basic wavefront LwiA. The emitted light from the condensing position control section 26 is incident on the beam splitter 28 through the lens 27, reflected by the beam splitter 28, and then reaches the first end surface 11a of the wavefront transmission unit 11 through the lens 29. The wavefront transmission unit 11 guides the incident light to the second end surface 11b by the respective cores, and emits the light from the second end surface 11b. The combined light Lco emitted from the second end surface 11b forms the light spot on the xy plane.

The incident wavefront on the first end surface 11a of the wavefront transmission unit 11 is obtained by the first tilt component being added to the basic wavefront LwiA, and the light spot is formed at a position corresponding to the first tilt component.

In the present embodiment, the basic wavefront modulator 22 emits the light having the same basic wavefront in a period during which an image for one screen is formed. On the other hand, the condensing position control section 26 changes the tilt component to be added to the basic wavefront LwiA at a predetermined cycle. For example, the condensing position control section 26 adds a second tilt component after the first tilt component. As a result, the incident wavefront on the first end surface 11a of the wavefront transmission unit 11 is obtained by the second tilt component being added to the basic wavefront LwiA, and the light spot is formed at a position corresponding to the second tilt component.

After that, the same operations are repeated, and the light spot formed on the xy plane by the combined light Lco emitted from the second end surface 11b moves in accordance with the tilt component added by the condensing position control section 26, and thereby the point scanning is performed within a predetermined range on the xy plane.

The reflected light from the object (object-reflected light) sequentially illuminated by the point scanning with the light spot is sequentially incident on the second end surface 11b of the wavefront transmission unit 11, and passes through the wavefront transmission unit 11, to be emitted from the first end surface 11a. The object-reflected light passes through the lens 29 and the beam splitter 28, to be incident on the detector 30. The detector 30 detects the light from the object, which is sequentially incident on the detector 30, and obtains an image signal based on the optical image of the object.

Note that the condensing position control section 23 adds the spherical component to the basic wavefront, to thereby be capable of moving the position where the light spot is formed in a direction perpendicular to the xy plane.

Thus, in the present embodiment, the basic wavefront modulator generates the light having the basic wavefront to form the light spot, and the condensing position control section adds the tilt component or the spherical component to the basic wavefront to change the condensing position of the light spot, to thereby achieve the point scanning. Therefore, the scanning rate of the point scanning depends on the speed of changing the adding amount of the tilt component by the condensing position control section. The condensing position control section is configured by the galvano mirror or the MEMS mirror, to thereby be capable of adding and changing the tilt component at an extremely high speed. As a result, extremely high speed scanning can be performed. With such a configuration, the present embodiment is capable of providing an image pickup apparatus which has a small size without including a distal end scanning mechanism and which is configured to pick up a high definition image at a high speed.

Second Embodiment

Figure 6:
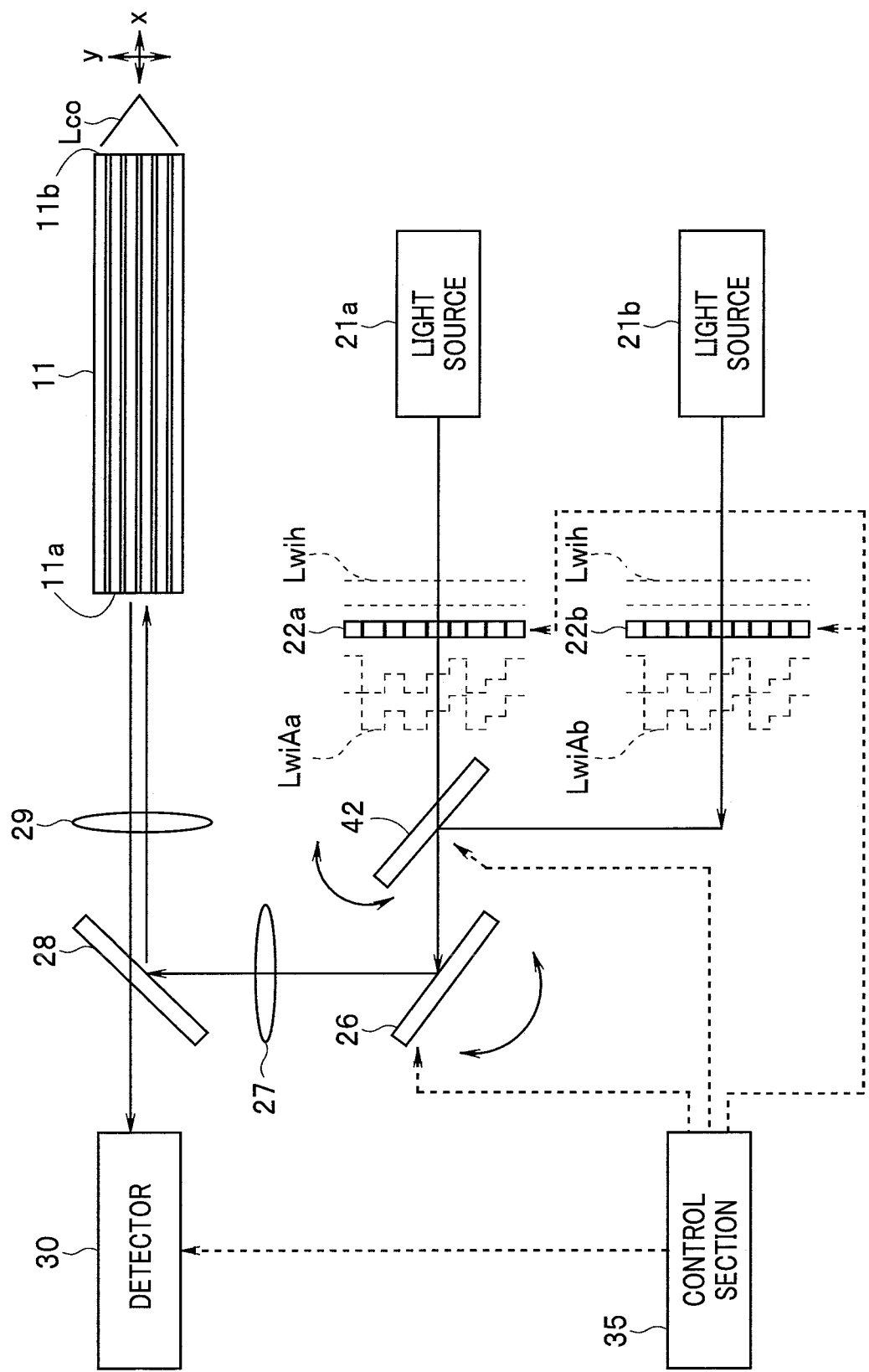
FIG. 6 is an explanatory view illustrating a second embodiment of the present invention.

FIG. 6 is an explanatory view illustrating the second embodiment of the present invention. In FIG. 6, the same constituent elements as those in FIG. 1 are attached with the same reference signs and descriptions thereof will be omitted.

In the first embodiment, the basic wavefront modulator 22 emits the light having the same basic wavefront in a scanning period for one screen. However, in a case where there are a few propagation modes in each of the cores of the wavefront transmission unit 11, in a case where there is a crosstalk between the cores, or in other cases, if the magnitude of the tilt component to be added to the basic wavefront (position modulation amount) becomes large, a distortion occurs in the light spot, which may result in a deterioration of the quality of image to be acquired. In addition, the aberrations generated by the optical systems (the lens 27 and the lens 29) that are provided for making the condensing position control section 26 conjugate to the first end surface 11a also change with the increase in the magnitude of the tilt component (position modulation amount) to be added to the basic wavefront, which also causes a distortion in the light spot. In view of such a circumstance, in the present embodiment, the basic wavefront is changed depending on the position of the screen so that the position modulation amount (the magnitude of the tilt component) to be added to the basic wavefront does not exceed a predetermined threshold.

For example, the basic wavefront modulator 22 can change the basic wavefront depending on the scanning position for each predetermined number of lines of one screen. However, in such a case, the scanning rate is affected by the frame rate of the basic wavefront modulator 22. Therefore, in the present embodiment, a plurality of basic wavefront modulators depending on the positions of the screen are prepared, and the basic wavefront modulator to be used is switched among the plurality of basic wavefront modulators, depending on the scanning position, to thereby enable high-speed point scanning.

Light sources 21a, 21b each have the same configuration as that of the light source 21 and emit generated light. A basic wavefront modulator 22a and a basic wavefront modulator 22b are disposed respectively on the optical path of the emitted light from the light source 21a and the optical path of the emitted light from the light source 21b. The basic wavefront modulators 22a, 22b each have the same configuration as that of the basic wavefront modulator 22. The basic wavefront modulators 22a, 22b are controlled by the control section 35, and convert the plane wave Lwih from the light source 21a and the plane wave Lwih from the light source 21b into the basic wave LwiAa and the basic wave LwiAb, respectively. Note that the basic wavefronts of the lights emitted from the basic wavefront modulator 22a and 22b correspond respectively to different positions of the screen. For example, the basic wavefront modulator 22a emits light having the basic wavefront LwiAa corresponding to a screen position on the upper side of the screen. The basic wavefront modulator 22b emits light having the basic wavefront LwiAb corresponding to a screen position on the lower side of the screen.

A wavefront switching member 42 is disposed on the optical path of the emitted light from each of the basic wavefront modulators 22a, 22b. Note that illustration of an optical system for guiding the emitted light from the basic wavefront modulator 22b to the wavefront switching member 42 is omitted. The wavefront switching member 42 is configured by a mirror, for example. The wavefront switching member 42 is controlled by the control section 35 so that the position thereof can be changed. In other words, the wavefront switching member 42 is disposed at a position other than a position on the optical path from the basic wavefront modulator 22a to the condensing position control section 26 to cause the emitted light from the basic wavefront modulator 22a to be incident on the condensing position control section 26, or disposed on the optical path of the emitted light from the basic wavefront modulator 22b to reflect the emitted light from the basic wavefront modulator 22b to cause the reflected light to be incident on the condensing position control section 26.

The control section 35 controls the wavefront switching member 42 in synchronization with the tilt component addition control, that is, point scanning control by the condensing position control section 26. In the case where the basic wavefront LwiAa from the basic wavefront modulator 22a corresponds to the upper side of the screen and the basic wavefront LwiAb from the basic wavefront modulator 22b corresponds to the lower side of the screen, for example, when the condensing position control section 26 performs point scanning control for the upper side of the screen, the control section 35 causes the wavefront switching member 42 to move such that the light from the basic wavefront modulator 22a is made to be incident on the condensing position control section 26. On the other hand, when the condensing position control section 26 performs point scanning control for the lower side of the screen, the control section 35 causes the wavefront switching member 42 to move such that the light from the basic wavefront modulator 22b is made to be incident on the condensing position control section 26.

Next, the operation of the embodiment thus configured will be described.

The light source 21a generates illumination light with the plane wave Lwih to cause the generated illumination light to be incident on the basic wavefront modulator 22a, and the light source 21b generates illumination light with the plane wave Lwih to cause the generated illumination light to be incident on the basic wavefront modulator 22b. The basic wavefront modulator 22a generates the light having the basic wavefront LwiAa corresponding to a predetermined first region on the screen. The basic wavefront modulator 22b generates the light having the basic wavefront LwiAb corresponding to a second region on the screen, the second region being different from the first region. When causing the condensing position control section 26 to add to the basic wavefront LwiAa the tilt component for performing point scanning for the first region, the control section 35 causes the wavefront switching member 42 to move such that the emitted light from the basic wavefront modulator 22a is made to be incident on the condensing position control section 26. On the other hand, when causing the condensing position control section 26 to add to the basic wavefront LwiAb the tilt component for performing point scanning for the second region, the control section 35 causes the wavefront switching member 42 to move such that the reflected light from the basic wavefront modulator 22b is made to be incident on the condensing position control section 26.

The basic wavefront LwiAa corresponds to the first region of the screen, and the magnitude of the tilt component to be added by the condensing position control section 26 for the point scanning for the relatively small first region is relatively small. Similarly, the basic wavefront LwiAb corresponds to the second region of the screen, and the magnitude of the tilt component to be added by the condensing position control section 26 for the point scanning for the relatively small second region is relatively small.

Thus, the magnitude of each of the tilt components to be added respectively to the basic wavefronts LwiAa and LwiAb by the condensing position control section 26 is relatively small. As a result, the distortion of the light spot obtained by the emitted light Lco from the wavefront transmission unit 11 is relatively small.

Thus, in the present embodiment, the basic wavefront is changed in accordance with the regions of the screen. The basic wavefronts corresponding respectively to the regions are prepared in advance, and either one of the wavefronts is selectively used in synchronization with the scanning control. Such a configuration has advantages of increasing the scanning rate and suppressing the distortion of the light spot.

Note that, in the present embodiment, description has been made on the example in which the screen is divided into two regions and the two basic wavefront modulators corresponding to the two regions of the screen are used. However, the screen may be divided into three or more regions, and three or more basic wavefront modulators corresponding respectively to the divided regions may be used.

Modifications

Figure 7:
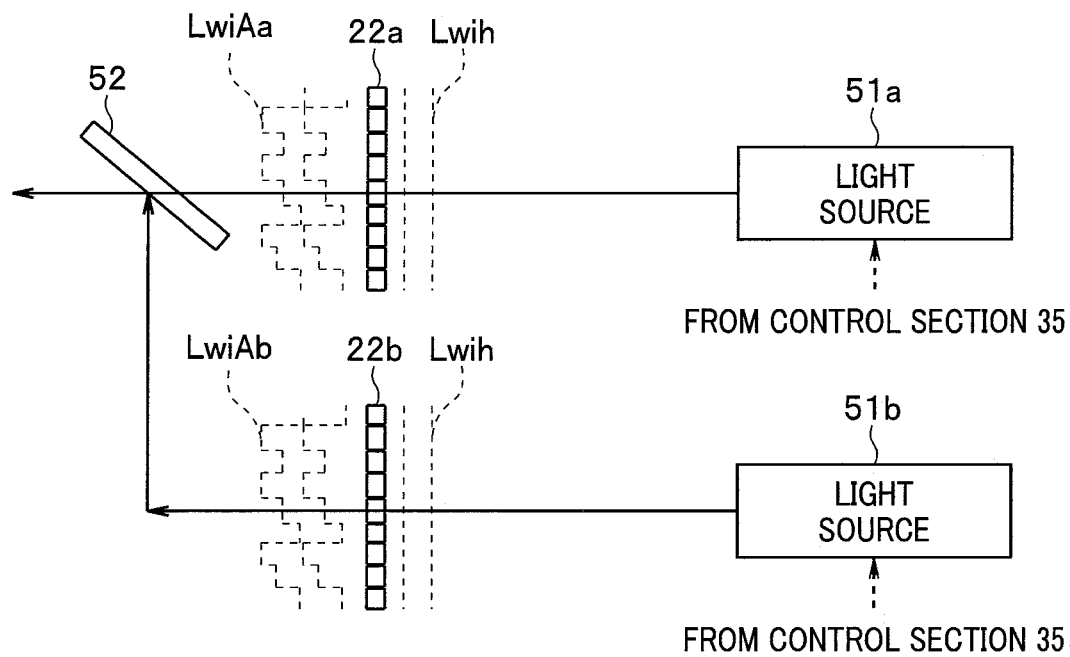
FIG. 7 is an explanatory view illustrating a modification of the second embodiment.
Figure 8:
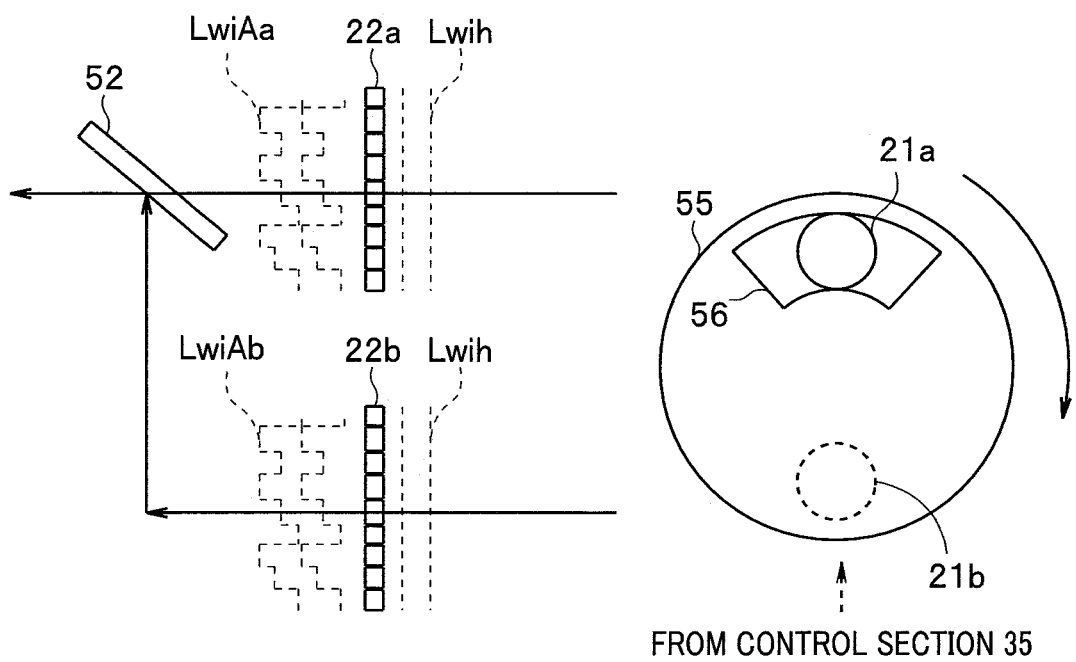
FIG. 8 is an explanatory view illustrating a modification of the second embodiment.

FIGS. 7 and 8 are explanatory views each illustrating a modification of the second embodiment. In the embodiment illustrated in FIG. 6, the wavefront switching member 42 is used, and the light having the basic wavefront LwiAa from the basic wavefront modulator 22a and the light having the basic wavefront LwiAb from the basic wavefront modulator 22b are selectively made to be incident on the condensing position control section 26. However, various methods can be considered for making two kinds of light each having the basic wavefront selectively incident on the condensing position control section 26.

The example illustrated in FIG. 7 is different from the embodiment illustrated in FIG. 6 only in that light sources Ma and Mb are used in place of the light sources 21a and 21b, respectively, and a beam splitter 52 is used in place of the wavefront switching member 42. Emission of illumination light from each of the light sources 51a, 51b is controlled by the control section 35. If it is supposed that the basic wavefront modulator 22a corresponds to the first region of the screen and the basic wavefront modulator 22b corresponds to the second region of the screen, the control section 35 performs control to turn on the light source 51a only in a period in which the condensing position control section 26 performs point scanning control for the first region of the screen and to turn on the light source 51b only in a period in which the condensing position control section 26 performs point scanning control for the second region of the screen.

The beam splitter 52 transmits the emitted light from the basic wavefront modulator 22a to cause the transmitted light to be incident on the condensing position control section 26 and reflects the emitted light from the basic wavefront modulator 22b to cause the reflected light to be incident on the condensing position control section 26. Note that illustration of an optical system for guiding the emitted light from the basic wavefront modulator 22b to the beam splitter 52 is omitted.

As a result, also in the example illustrated in FIG. 7, the light having the basic wavefront LwiAa is incident on the condensing position control section 26 in the period in which the condensing position control section 26 performs the point scanning control for the first region of the screen, and the light having the basic wavefront LwiAb is incident on the condensing position control section 26 in the period in which the condensing position control section 26 performs the point scanning control for the second region of the screen.

FIG. 8 illustrates an example in which an emitted light switching member 55 is used. The emitted light switching member 55 is a disk-shaped member and includes, at a part near the periphery thereof, an opening portion 56. The emitted light switching member 55 is controlled by the control section 35, and configured to be rotatable, with a center of a circular shape as a rotational axis, as illustrated by the arrow in FIG. 8. Under the rotation control by the control section 35, the emitted light switching member 55 can rotate to a position where the opening portion 56 allows the emitted light from the light source 21a to pass through, and can rotate also to a position where the opening portion 56 allows the emitted light from the light source 21b to pass through. FIG. 8 illustrates a state where the light from the light source 21a can be incident on the basic wavefront modulator 22a, for example.

If it is supposed that the basic wavefront modulator 22a corresponds to the first region of the screen and the basic wavefront modulator 22b corresponds to the second region of the screen, the control section 35 controls the rotation of the emitted light switching member 55 such that the light from the light source 21a is emitted to the basic wavefront modulator 22a through the opening portion 56 in the period in which the condensing position control section 26 performs the point scanning control for the first region of the screen and the light from the light source 21b is emitted to the basic wavefront modulator 22b through the opening portion 56 in the period in which the condensing position control section 26 performs the point scanning control for the second region of the screen.

As a result, also in the example illustrated in FIG. 8, the light having the basic wavefront LwiAa is incident on the condensing position control section 26 in the period in which the condensing position control section 26 performs the point scanning control for the first region of the screen, and the light having the basic wavefront LwiAb is incident on the condensing position control section 26 in the period in which the condensing position control section 26 performs the point scanning control for the second region of the screen. Note that the emitted light switching member 55 is provided with the one opening portion 56 in the above-described embodiment. However, the emitted light switching member 55 may include on the circumference thereof a plurality of opening portions.

Third Embodiment

Figure 9:
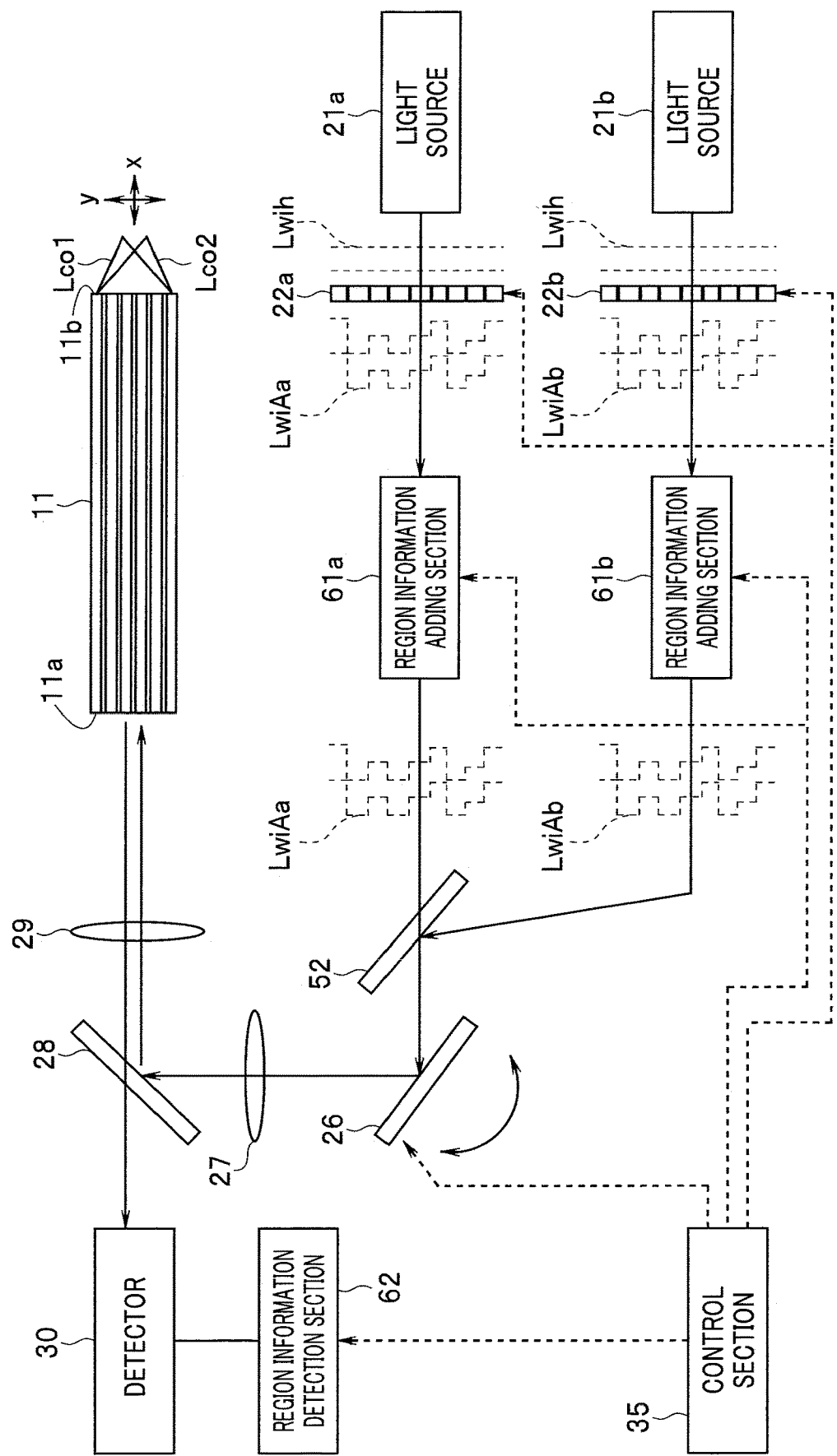
FIG. 9 is an explanatory view illustrating a third embodiment of the present invention.

FIG. 9 is an explanatory view illustrating the third embodiment of the present invention. In FIG. 9, the same constituent elements as those in FIGS. 6 and 7 are attached with the same reference signs and descriptions thereof will be omitted.

In the second embodiment, the scanning for one screen is performed by dividing the one screen into a plurality of regions, and adding the tilt component to the basic wavefront corresponding to each of the divided regions by the condensing position control section 26 while selecting the light having the basic wavefront corresponding to each of the divided regions in accordance with the scanning position by the condensing position control section 26. In contrast, in the present embodiment, the lights respectively having the basic wavefronts corresponding respectively to the regions are used simultaneously, and light spots are simultaneously formed in a plurality of regions by the addition of the tilt component by the condensing position control section 26, to thereby enable point scanning to be performed with the light spots. Note that, in this case, the respective basic wavefronts corresponding to the respective regions form the light spots at positions on the xy plane that correspond to the respective regions. In such a configuration, the same tilt component is simultaneously added to these basic wavefronts, to thereby enable point scanning to be executed simultaneously at the positions corresponding to the respective regions. Accordingly, the time required for the scanning for the one screen is the time required for one in the number of divided regions of the screen, compared with the case where the screen is not divided into regions.

However, when such illumination is applied to the image pickup apparatus, it is necessary to identify to which position on the screen the reflected light from an object corresponds. Therefore, in the present embodiment, region information adding sections 61a and 61b are provided. The region information adding section 61a, which is a first information adding apparatus, is controlled by the control section 35 and configured to emit the light having the basic wavefront from the basic wavefront modulator 22a by adding information indicating the first region of the screen to the light. The region information adding section 61b, which is a second information adding apparatus, is controlled by the control section 35 and configured to emit the light having the basic wavefront from the basic wavefront modulator 22b by adding information indicating the second region of the screen to the light.

The emitted light from the region information adding section 61a passes through the beam splitter 52 to be incident on the condensing position control section 26. The emitted light from the region information adding section 61b is reflected by the beam splitter 52 to be incident on the condensing position control section 26. Note that FIG. 9 illustrates an example in which the screen is divided into two regions. However, the screen is divided into three or more regions. In such a case, the light sources, the basic wavefront modulators, and the region information adding sections may be provided in the same number as that of the divided regions.

The region information adding sections 61a and 61b add the pieces of information indicating the respective regions by changing the characteristics of the incident lights without performing processing for changing the basic wavefronts. The region information adding sections 61a, 61b add the pieces of information by changing the intensities or the wavelengths of the incident lights. For example, the region information adding sections 61a, 61b may cause the incident lights to flicker by changing the intensities of the incident lights and may add the pieces of information on the respective regions by making flickering frequencies, flickering phases, or flickering intensities differ from each other. Furthermore, the region information adding sections 61a, 61b may add the pieces of information on the regions by making the wavelengths of the incident lights differ from each other, for example.

For example, if mechanical shutters, AO modulators (Acoust Optical Modulators), and the like are used as the region information adding sections 61a, 61b, it is possible to cause the incident lights to flicker, and control the flickering frequencies, flickering phases, or flickering intensities of the incident lights. Furthermore, if color filters are used, for example, as the region information adding sections 61a, 61b, it is possible to change the wavelengths of the incident lights. Thus, the region information adding sections 61a, 61b are capable of emitting flickering lights or the lights whose wavelengths are changed, without changing the basic wavefronts of the lights.

A region information detection section 62, as a region information detection apparatus, is configured to receive, from the control section 35, the information on each of the regions added by each of the region information adding sections 61a, 61b. Based on the information received from the control section 35, the region information detection section 62 is configured to be capable of separating and detecting the object-reflected light in each of the positions corresponding to the respective regions from the light detected by the detector 30.

Figure 10A:
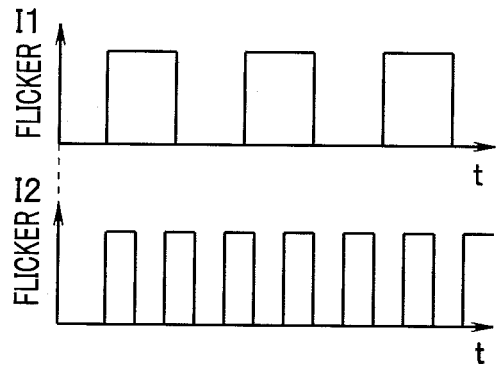
FIG. 10A is an explanatory view for describing an operation of the third embodiment.
Figure 10B:
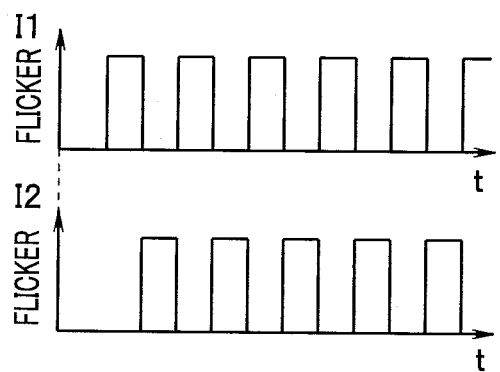
FIG. 10B is an explanatory view for describing an operation of the third embodiment.
Figure 10C:
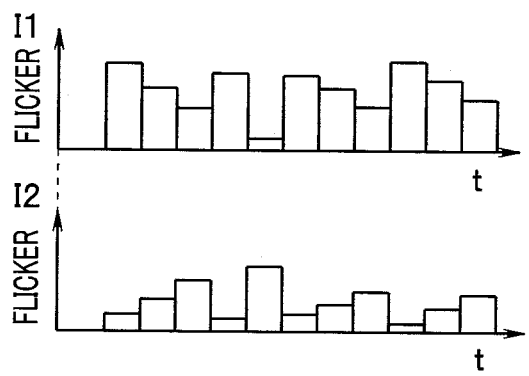
FIG. 10C is an explanatory view for describing an operation of the third embodiment.

Next, the operation of the embodiment thus configured will be described with reference to the explanatory views in FIGS. 10A to 10C. FIGS. 10A to 10C each describe the information added by the region information adding section 61. In each of FIGS. 10A to 10C, the horizontal axis represents time t, the vertical axis I1 represents the light intensity of the emitted light from the region information adding section 61a, and the vertical axis I2 represents the light intensity of the emitted light from the region information adding section 61b. Thus, FIGS. 10A to 10C each illustrate the example in which the information on each of the regions is transmitted by changing the light intensities.

The plane wave from the light source 21a is converted into light having a basic wavefront (first basic wavefront) corresponding to a predetermined position in the first region by the basic wavefront modulator 22a, to be incident on the condensing position control section 26 through the region information adding section 61a and the beam splitter 52. Furthermore, the plane wave from the light source 21b is converted into light having a basic wavefront (second basic wavefront) corresponding to a predetermined position in the second region, the predetermined position corresponding to the predetermined position in the first region, by the basic wavefront modulator 22b, to be incident on the condensing position control section 26 through the region information adding section 61b and the beam splitter 52.

The region information adding sections 61a, 61b do not change the wavefronts, and the light having the first basic wavefront and the light having the second basic wavefront, the positions of which are controlled by the addition of the tilt component by the condensing position control section 26, are incident on the first end surface 11a of the wavefront transmission unit 11. Thus, the emitted light Lco1 based on the first basic wavefront and the emitted light Lco2 based on the second wavefront are emitted from the second end surface 11b of the wavefront transmission unit 11. As a result, the light spot based on the emitted light Lco1 and the light spot based on the emitted light Lco2 are simultaneously formed at the positions corresponding respectively to the first and second regions.

Now it is supposed that the control illustrated in FIG. 10A is performed by the control section 35 in the region information adding sections 61a, 61b, for example. FIG. 10A illustrates that the emitted light from the basic wavefront modulator 22a is caused to flicker at a predetermined frequency, e.g., a frequency f1 in the region information adding section 61a. In addition, FIG. 10A illustrates that the emitted light from the basic wavefront modulator 22b is caused to flicker at a predetermined frequency, e.g., a frequency f2, which is different from f1, in the region information adding section 61b. Note that the frequencies f1, f2 are sufficiently higher than the scanning rate. The flickering of each of the light spots is repeated in the period in which each of the light spots is formed in one position in each of the regions corresponding respectively to the first region and the second region.

The object-reflected light formed by the light spot based on the emitted light Lco1 and the object-reflected light formed by the light spot based on the emitted light Lco2 are incident from the second end surface 11b, pass through the wavefront transmission unit 11 to be emitted from the first end surface 11a, and then pass through the lens 29 and the beam splitter 28 to be incident on the detector 30. The light detected by the detector 30 includes the component of the light that flickers at the frequency f1 and the component of the light that flickers at the frequency f2. The region information detection section 62 receives information on each of the frequencies f1, f2 from the control section 35. The region information detection section 62 separates the component of the light that flickers at the frequency f1 and the component of the light that flickers at the frequency f2 from the light detected by the detector 30, and detects the levels of the separated components. The detected levels indicate the levels of the object-reflected light from the region corresponding to the first region and the object-reflected light from the region corresponding to the second region.

Thus, the lights having the basic wavefronts are caused to flicker by the region information adding sections 61a, 61b, and the flickering frequencies are made to differ from each other by the region information adding sections 61a, 61b, to thereby enable the level of object-reflected light from the region corresponding to the first region and the level of the object-reflected light from the region corresponding to the second region to be detected separately from the detection result by the detector 30.

It is supposed that the control illustrated in FIG. 10B is performed by the control section 35 in the region information adding sections 61a, 61b, for example. FIG. 10B illustrates that the light having the first basic wavefront and the light having the second basic wavefront corresponding respectively to the corresponding positions in the first region and the second region are caused to flicker and the flickering phases are made to differ from each other by the region information adding sections 61a, 61b. The flickering frequencies are sufficiently higher than the scanning rate. The flickering of each of the light spots is repeated in the period in which each of the light spots is formed in one position in each of the regions corresponding respectively to the first region and the second region. Note that, in the example illustrated in FIG. 10B, the emitted light Lco1 and the emitted light Lco2 are generated alternately, and the light spot is formed alternately in the region corresponding to the first region and in the region corresponding to the second region.

Therefore, the object-reflected light from the region corresponding to the first region and the object-reflected light from the region corresponding to the second region are alternately incident on the detector 30. The region information detection section 62 receives the information on each of the flickering phases from the control section 35. The region information detection section 62 is capable of detecting the level of the object-reflected light from the region corresponding to the first region and the level of the object-reflected light from the region corresponding to the second region separately.

Thus, the lights having the basic wavefronts are caused to flicker by the region information adding sections 61a and 61b, and the flickering phases are made to differ from each other by the region information adding sections 61a and 61b, to thereby enable the level of the object-reflected light from the region corresponding to the first region and the level of the object-reflected light from the region corresponding to the second region to be detected separately from the detection result obtained by the detector 30.

Note that, when the control illustrated in FIG. 10B is performed, two detectors may be prepared and the detector that receives the object-reflected light may be selected from the two detectors in synchronization with the flickering timing.

Furthermore, it is supposed that the control illustrated in FIG. 10C is performed by the control section 35 in the region information adding sections 61a, 61b, for example. FIG. 10C illustrates that the intensity of the emitted light from the basic wavefront modulator 22a is changed in a predetermined first pattern in the region information adding section 61a. In addition, FIG. 10C illustrates that the intensity of the emitted light from the basic wavefront modulator 22b is changed in a predetermined second pattern different from the first pattern in the region information adding section 61b. The frequencies of the intensity changes are sufficiently higher than the scanning rate, and the intensity of the light spot changes in the first pattern or the second pattern in the period in which each of the light spots is formed in one position in each of the regions corresponding respectively to the first region and the second region.

The light detected by the detector 30 includes a component of the light the level of which changes in the first pattern and a component of the light the level of which changes in the second pattern. The region information detection section 62 receives the information on the first pattern and the information on the second pattern from the control section 35. The region information detection section 62 separates the component of the light the level of which changes in the first pattern and the component of the light the level of which changes in the second pattern from the light detected by the detector 30, and detects the levels of the separated components. The detected levels indicate the level of the object-reflected light from the region corresponding to the first region and the level of the object-reflected light from the region corresponding to the second region.

The intensity of the light having the basic wavefront is thus controlled by each of the region information adding sections 61a, 61b, to thereby generate the light the intensity of which changes in the first pattern or the light the intensity of which changes in the second pattern. With such a configuration, it is possible to detect the level of the object-reflected light from the region corresponding to the first region and the level of the object-reflected light from the region corresponding to the second region separately from the detection result obtained by the detector 30.

Thus, in the present embodiment, the intensities and the wavelengths are changed in the light having the basic wavefront corresponding to the first region and the basic wavefront corresponding to the second region by the region information adding sections, to thereby enable the level of the object-reflected light from the region corresponding to the first region and the level of the object-reflected light from the region corresponding to the second region to be detected separately from the detection result obtained by the detector. When the wavelengths are changed, detectors corresponding to the respective wavelengths may be provided. In such a case, it is possible to detect the level of the object-reflected light from the region corresponding to the first region and the level of the object-reflected light from the region corresponding to the second region based on the outputs from the respective detectors.

Modifications

Figure 11:
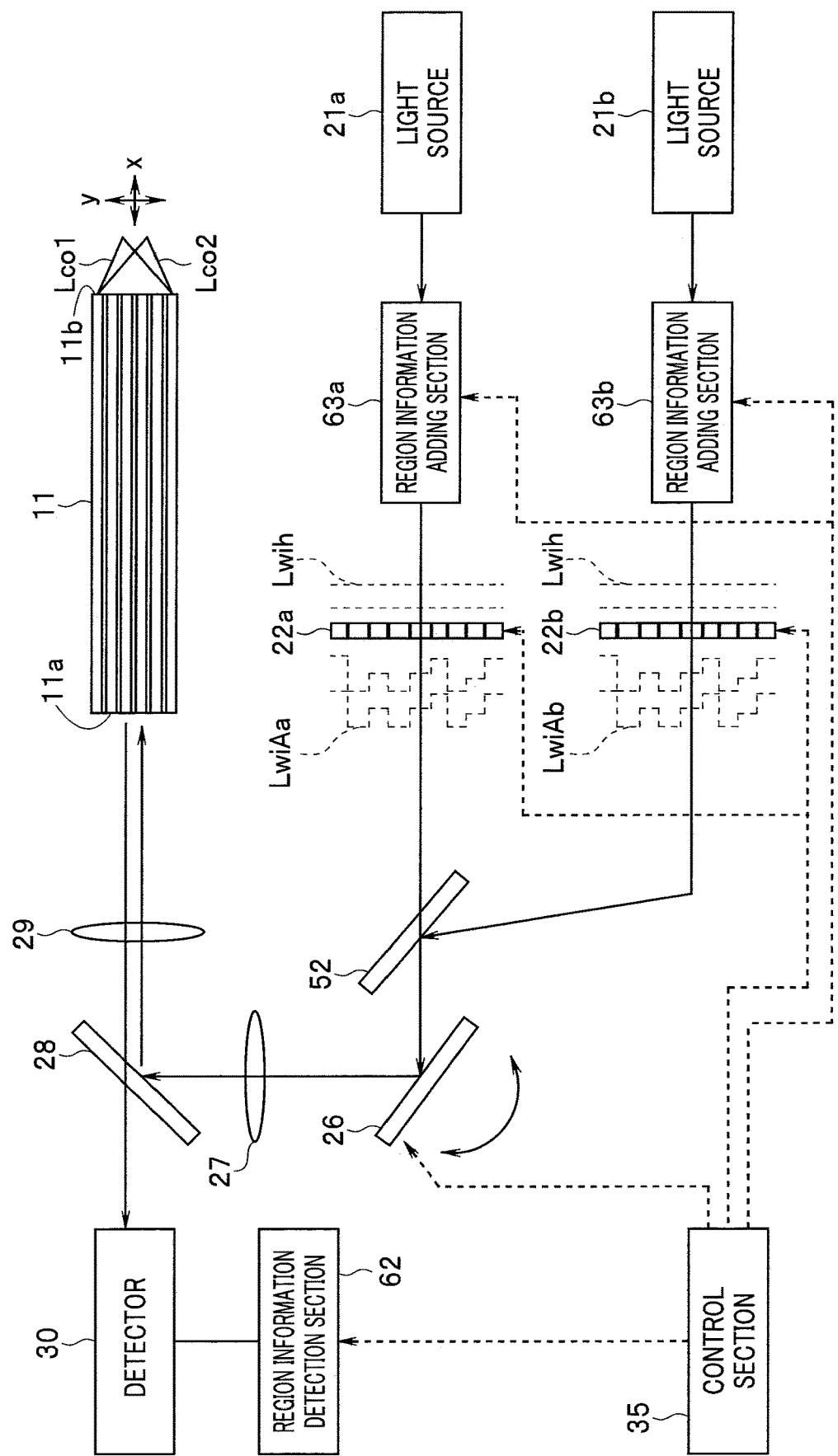
FIG. 11 is an explanatory view illustrating a modification of the third embodiment.
Figure 12:
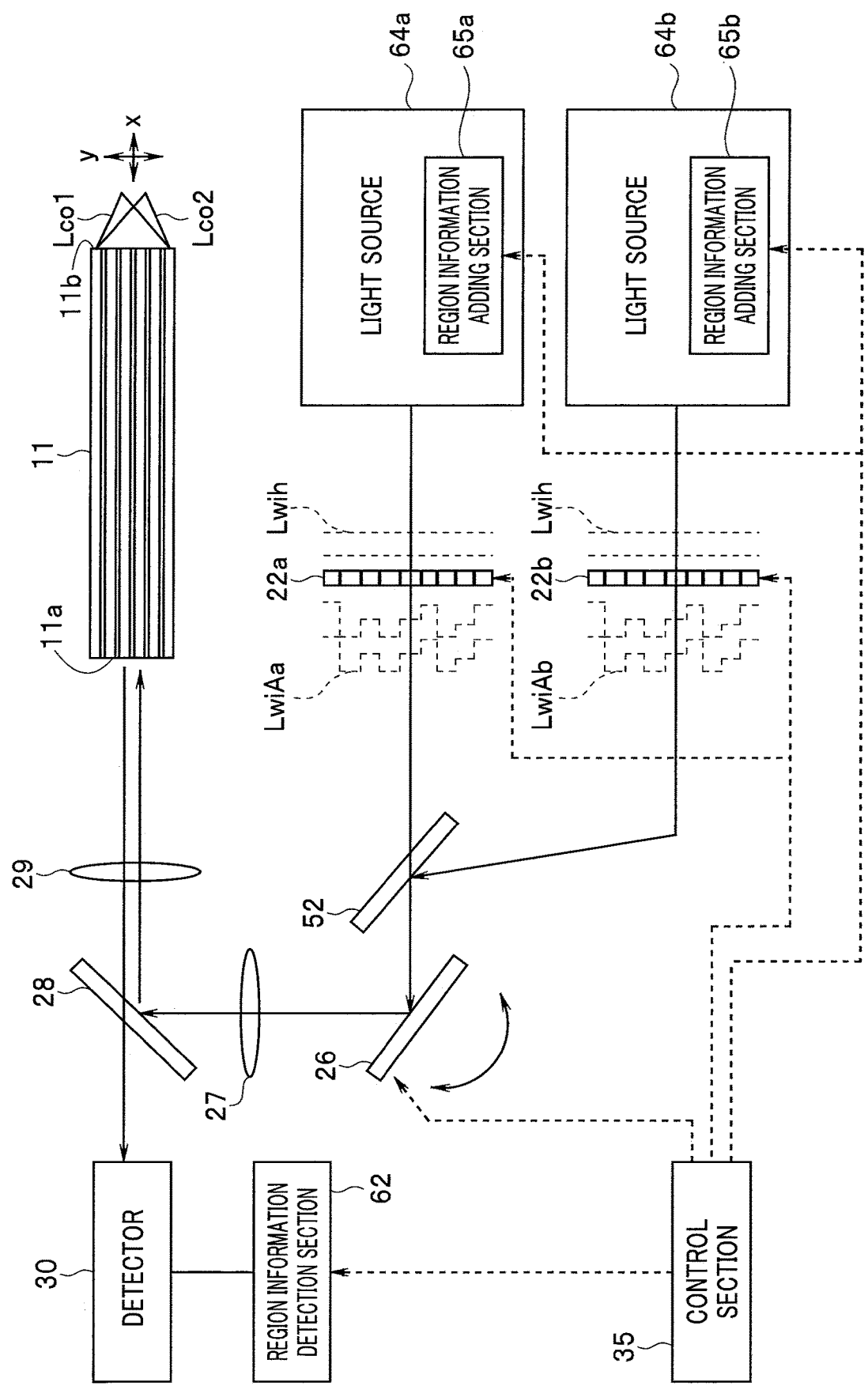
FIG. 12 is an explanatory view illustrating a modification of the third embodiment.

FIGS. 11 and 12 are explanatory views each illustrating a modification of the third embodiment.

In FIG. 9, the region information adding section 61*a* is disposed on the optical path of the emitted light from the basic wavefront modulator 22*a* and the region information adding section 61*b* is disposed on the optical path of the emitted light from the basic wavefront modulator 22*b*. In contrast, in the modification illustrated in FIG. 11, a region information adding section 63*a* is disposed on the optical path from the light source 21*a* to the basic wavefront modulator 22*a* and a region information adding section 63*b* is disposed on the optical path from the light source 21*b* to the basic wavefront modulator 22*b*. The region information adding sections 63*a*, 63*b* respectively have the same configurations as those of the region information adding sections 61*a*, 61*b*. In other words, the region information adding section 63*a* is controlled by the control section 35, and configured to emit the light with the plane wave from the light source 21*a* by adding the information indicating the first region of the screen to the light. The region information adding section 63*b* is controlled by the control section 35, and configured to emit the light with the plane wave from the light source 21*b* by adding the information indicating the second region of the screen to the light.

The light from the region information adding section 63*a* is incident on the basic wavefront modulator 22*a* to be converted into the light having the first basic wavefront corresponding to a predetermined position in the first region. The light from the region information adding section 63*b* is incident on the basic wavefront modulator 22*b* to be converted into the light having the second basic wavefront corresponding to a predetermined position in the second region, which corresponds to the predetermined position in the first region.

Similarly as the region information adding sections 61*a*, 61*b*, the region information adding sections 63*a*, 63*b* add pieces of information indicating the respective regions by changing the characteristics of the incident lights without changing the wavefronts. For example, the region information adding sections 63*a*, 63*b* change the intensities or the wavelengths of the incident lights. For example, similarly as the region information adding sections 61*a*, 61*b*, the region information adding sections 63*a*, 63*b* cause the incident lights to flicker by changing the intensities of the incident lights, and make the flickering frequencies, flickering phases, or flickering intensities of the incident lights differ from each other, or make the wavelengths of the incident lights differ from each other.

Thus, the example illustrated in FIG. 11 is also capable of providing the same working and effects as those in the third embodiment.

The example illustrated in FIG. 12 uses light sources 64*a* and 64*b* including region information adding sections 65*a*, 65*b*, respectively. In the example illustrated in FIG. 11, the region information adding sections 63*a*, 63*b* cause the incident lights to flicker by changing the intensities of the incident lights, for example, and emit the lights whose flickering frequencies, flickering phases, or flickering intensities differ from each other, or emit the lights whose wavelengths differ from each other. Such lights can also be emitted from the light sources 64*a*, 64*b*. In other words, the region information adding sections 65*a*, 65*b* are controlled by the control section 35 to control the emitted lights from the light sources 64*a*, 64*b*, and cause the lights to flicker and emit the lights whose flickering frequencies, flickering phases, or flickering intensities differ from each other, or emit the lights whose wavelengths differ from each other, for example.

Thus, the example illustrated in FIG. 12 is also capable of providing the same working and effects as those in the third embodiment.

Fourth Embodiment

Figure 13:
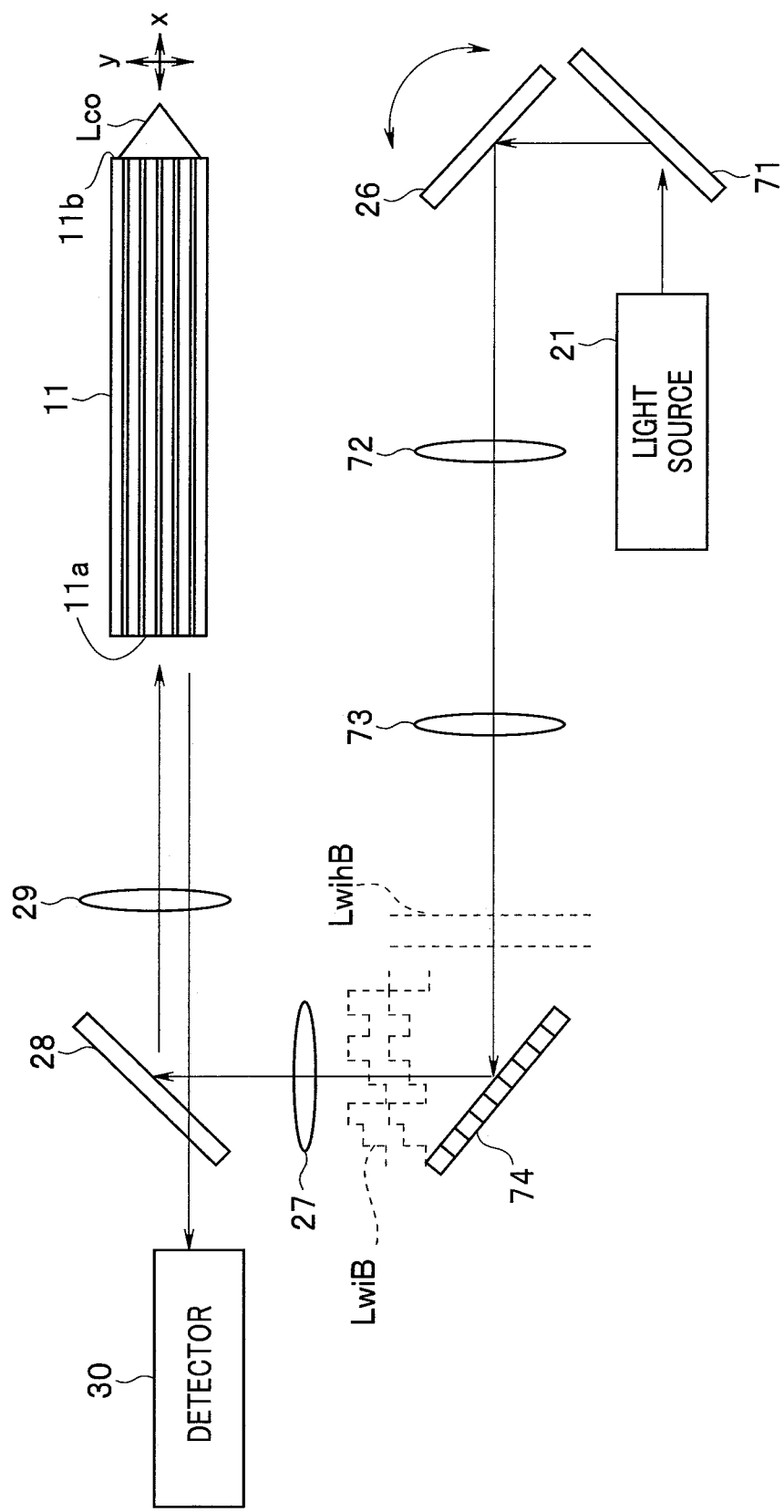
FIG. 13 is an explanatory view illustrating a fourth embodiment of the present invention.

FIG. 13 is an explanatory view illustrating the fourth embodiment of the present invention. In FIG. 13, the same constituent elements as those in FIG. 1 are attached with the same reference signs and descriptions thereof will be omitted. The present embodiment is different from the first embodiment in that the emitted light from the light source 21 is made to be incident on the condensing position control section 26 and the emitted light from the condensing position control section 26 is made to be incident on a basic wavefront modulator 74.

The emitted light from the light source 21 is incident on the condensing position control section 26 through a mirror 71. The condensing position control section 26 emits the light by adding a tilt component to the light. Lenses 72, 73, and the basic wavefront modulator 74 are disposed on the optical axis of the emitted light from the condensing position control section 26. The basic wavefront modulator 74 is a reflective spatial light phase modulator configured to reflect the incident light and change the wavefront of the incident light.

The basic wavefront modulator 74 is configured by a spatial light phase modulator such as a reflective liquid crystal array (LCOS) in which a plurality of pixels are arranged two-dimensionally, for example. The basic wavefront modulator 74 is configured such that the number of pixels in the array is equal to or larger than at least the number of cores that configure the wavefront transmission unit 11. The basic wavefront modulator 74 is controlled by the control section 35 and configured to change retardation of the respective pixels in the array within a phase delay (retardation) of 0 to $2\pi$ in a desired gradation. When the basic wavefront modulator 74 is configured by a liquid crystal array, polarization components to which retardation can be applied are limited. Therefore, the polarization of the light from the condensing position control section 26 may be limited in a direction in which retardation can be changed.

The condensing position control section 26, the basic wavefront modulator 74, and the first end surface 11a are disposed at the positions optically conjugate to one another.

In the present embodiment thus configured, the light source 21 emits the plane wave, and the condensing position control section 26 adds the tilt component to the received plane wave, to emit the resultant plane wave. The basic wavefront modulator 74 receives, on the incident surface thereof, the plane wave LwihB to which the tilt component is added, and emits the light having the basic wavefront LwiB for forming the light spot at a position with a predetermined distance from the second end surface 11b of the wavefront transmission unit 11, on the plane (xy plane) that is parallel to the second end surface 11b, for example. The position of the light spot on the xy plane is determined by the tilt component added by the condensing position control section 26.

Other workings are the same as those in the first embodiment.

Thus, the present embodiment is also capable of providing the same effects as those in the first embodiment.

Note that, in the respective embodiments as described above, occurrence of bending in the wavefront transmission unit 11 is not taken into consideration. Therefore, a fiber Bragg grating may be added to the wavefront transmission unit 11 to detect the bending of the wavefront transmission unit 11, and based on the detection result of the bending, a picked-up image in which an influence of the bending is corrected may be obtained by correcting or joining the optical images incident through the second end surface. In such a case, a range larger than a screen of the image to be configured may be scanned by taking the correction of the bending into consideration.

The present invention is not limited to the above-described embodiments as they are, and it goes without saying to embody the invention by modifying the constituent elements in a range without departing from the gist of the invention at the practical stage. In addition, various inventions can be achieved by appropriately combining the plurality of constituent elements disclosed in each of the above-described embodiments. Some of the constituent elements may be deleted from all the constituent elements shown in the embodiments, for example. Furthermore, constituent elements over different embodiments may be appropriately combined.

What is claimed is:

1. An optical scanning apparatus comprising:
   a fiber comprising a plurality of cores, the fiber being configured to transmit light between a first end surface of the fiber and a second end surface of the fiber,
      wherein the first end surface of the fiber is configured by one end surface of the plurality of cores, and the second end surface of the fiber is configured by another end surface of the plurality of cores; and
      wherein a first light having an incident wavefront which is a plane wave incident on the first end surface of the fiber exits from the second end surface of the fiber as a second light having a second wavefront due to relative phase differences among the plurality of cores, the second light having a random intensity distribution;
   a light source configured to emit a light;
   a basic wavefront modulator configured to perform spatial light phase modulation on the light emitted from the light source to be incident on the first end surface of the fiber, such that the light to be incident on the first end surface of the fiber has a basic wavefront that offsets the relative phase difference among the plurality of cores and is transmitted by the fiber to exit from the second end surface of the fiber as illumination light having a basic intensity distribution at a position with a predetermined distance from the second end surface of the fiber, and having a predetermined intensity pattern; and
   a two-dimensional intensity distribution control apparatus configured to be controlled to change the basic intensity distribution of the light having the basic wavefront to thereby cause a position of the predetermined intensity pattern to shift.

2. The optical scanning apparatus according to claim 1, wherein the two-dimensional intensity distribution control apparatus is configured to be controlled to change the basic intensity distribution of the light having the basic wavefront by adding a tilt component to the basic wavefront.

3. The optical scanning apparatus according to claim 1, wherein the two-dimensional intensity distribution control apparatus comprises a mirror configured to change a reflection direction of incident light.

4. The optical scanning apparatus according to claim 1, wherein the two-dimensional intensity distribution control apparatus comprises:
   a lens configured to cause light to be incident on the first end surface of the fiber; and
   a mirror configured to reflect the light having the basic wavefront to be incident on the lens, and to change an incident position on the lens of the light having the basic wavefront, to thereby add a tilt component to the basic wavefront.

5. The optical scanning apparatus according to claim 1, further comprising,
   a depth direction intensity distribution control apparatus configured to be controlled to add a spherical component to the basic wavefront to cause the basic intensity distribution to move in a direction orthogonal to the second end surface of the fiber.

6. The optical scanning apparatus according to claim 1, wherein the basic wavefront modulator comprises:
   a first basic wavefront modulator configured to perform spatial light phase modulation on the light emitted from the light source, such that the light to be incident on the first end surface of the fiber has a first basic wavefront and is transmitted by the fiber to exit from the second end surface of the fiber as first illumination light having a basic intensity distribution in a first region with a first predetermined distance from the second end surface of the fiber; and
   a second basic wavefront modulator configured to perform spatial light phase modulation on the light emitted from the light source, such that the light to be incident on the first end surface of the fiber has a second basic wavefront and is transmitted by the fiber to exit from the second end surface of the fiber as second illumination light having a basic intensity distribution in a second region with a second predetermined distance from the second end surface of the fiber, and
   wherein the optical scanning apparatus further comprises an optical system configured to cause the light having the first basic wavefront and the light having the second basic wavefront to be incident on the two-dimensional intensity distribution control apparatus while switching between the light having the first basic wavefront and the light having the second basic wavefront.

7. The optical scanning apparatus according to claim 1, wherein the basic wavefront modulator comprises:
- a first basic wavefront modulator configured to perform spatial light phase modulation on the light emitted from the light source, such that the light to be incident on the first end surface of the fiber has a first basic wavefront and is transmitted by the fiber to exit from the second end surface of the fiber as first illumination light having a basic intensity distribution at a first position in a first region with a first predetermined distance from the second end surface of the fiber; and
- a second basic wavefront modulator configured to perform spatial light phase modulation on the light emitted from the light source, such that the light to be incident on the first end surface of the fiber has a second basic wavefront and is transmitted by the fiber to exit from the second end surface of the fiber as second illumination light having a basic intensity distribution at a second position in a second region with a second predetermined distance from the second end surface of the fiber, the second position corresponding to the first position, and wherein the optical scanning apparatus further comprises:
- a first region information adding apparatus configured to add information indicating the first region to the light having the first basic wavefront; and
- a second region information adding apparatus configured to add information indicating the second region to the light having the second basic wavefront.

8. An image pickup apparatus comprising:
the optical scanning apparatus according to claim 7;
a photoelectric conversion apparatus configured to receive at least one of reflected light and fluorescence from an object illuminated with the illumination light exited from the second end surface of the fiber and convert the at least one of the reflected light and the fluorescence into an electric signal; and
a region information detection apparatus configured to detect an electric signal based on light from the first region and an electric signal based on light from the second region separately, based on the information added by the first region information adding apparatus and the information added by the second region information adding apparatus.

9. The optical scanning apparatus according to claim 1, wherein the two-dimensional intensity distribution control apparatus has a relationship optically conjugate to the first end surface of the fiber, and is configured to be controlled to change the basic intensity distribution of the light having the basic wavefront to add a tilt component to the basic wavefront to be incident on the first end surface of the fiber.

10. The optical scanning apparatus according to claim 1, wherein the two-dimensional intensity distribution control apparatus has a relationship optically conjugate to the first end surface of the fiber, and is configured to be controlled to change the basic intensity distribution of the light having the basic wavefront to add a tilt component to the basic wavefront to cause a plane wave of the light emitted by the light source to be incident on the first end surface of the fiber.

11. An image pickup apparatus comprising:
the optical scanning apparatus according to claim 1; and
a photoelectric conversion apparatus configured to receive at least one of reflected light and fluorescence from an object illuminated with the illumination light exited from the second end surface of the fiber and convert the at least one of the reflected light and the fluorescence into an electric signal.

12. The image pickup apparatus according to claim 11, wherein the photoelectric conversion apparatus is configured to receive the at least one of the reflected light and the fluorescence from the object through the first end surface of the fiber.

13. The optical scanning apparatus according to claim 1, wherein setting of the basic wavefront modulator is not changed, during a period in which the two-dimensional intensity distribution control apparatus changes the basic intensity distribution of the light having the basic wavefront, to thereby cause the position of the predetermined intensity pattern to shift and form an image for one screen.

14. The optical scanning apparatus according to claim 1, further comprising:
a controller configured to at least control the two-dimensional intensity distribution control apparatus to change the basic intensity distribution of the light having the basic wavefront.

* * * * *